United States Patent [19]

Ife et al.

[11] Patent Number: 5,409,943
[45] Date of Patent: Apr. 25, 1995

[54] [(ALKOXY)PYRIDINYL]AMINE COMPOUNDS WHICH ARE USEFUL IN THE TREATMENT OF GASTROINTESTINAL DISORDERS

[75] Inventors: Robert J. Ife; Colin A. Leach, both of Stevenage; Dashyant Dhanak, Biggleswade, all of England

[73] Assignee: SmithKline Beecham Intercredit B.V., Netherlands

[21] Appl. No.: 256,697

[22] PCT Filed: Jan. 26, 1993

[86] PCT No.: PCT/EP93/00174
§ 371 Date: Jul. 20, 1994
§ 102(e) Date: Jul. 20, 1994

[87] PCT Pub. No.: WO93/15055
PCT Pub. Date: Aug. 5, 1993

[30] Foreign Application Priority Data

Jan. 27, 1992 [GB] United Kingdom ............... 9201693

[51] Int. Cl.$^6$ ............... C07D 213/75; A61K 31/44
[52] U.S. Cl. ............... 514/349; 546/297
[58] Field of Search ............... 546/297; 514/349

[56] References Cited

FOREIGN PATENT DOCUMENTS

| | | | |
|---|---|---|---|
| 0055179 | 6/1982 | European Pat. Off. | 546/297 |
| 0204285 | 12/1986 | European Pat. Off. | 546/113 |
| 0268989 | 6/1988 | European Pat. Off. | 546/113 |
| 2439299 | 3/1975 | Germany | 546/297 |
| 1444558 | 8/1976 | United Kingdom | 546/297 |

OTHER PUBLICATIONS

Michael J. Dimsdale, "The Synthesis of 3-and 5-Amino-1,2,4-Oxadiazoles, A Caveat", *J. Heterocyclic Chem,* 18:37-41 (1981).

*Primary Examiner*—C. Warren Ivy
*Assistant Examiner*—Zinna N. Davis
*Attorney, Agent, or Firm*—Linda E. Hall; Stuart R. Suter; Edward T. Lentz

[57] ABSTRACT

The present invention relates to N-pyridylamidine and N-pyridylguanidine derivatives of general formula (I) in which: $Ar^1$ is an optionally substituted phenyl ring; $Ar^2$ is an optionally substituted phenyl ring; $R^1$ is hydrogen or $C_{1-4}$alkyl; $R^2$ is hydrogen or $C_{1-4}$alkyl; $R^3$ is hydrogen or $C_{1-4}$alkyl; $R^4$ is hydrogen, halogen, $C_{1-6}$alkyl or $C_{1-6}$alkoxy; X is $CH_2$ or $NR^5$, and $R^5$ is hydrogen or $C_{1-4}$alkyl, and the salts thereof, and their use in therapy as gastric acid secretion inhibitors.

6 Claims, No Drawings

[(ALKOXY)PYRIDINYL]AMINE COMPOUNDS WHICH ARE USEFUL IN THE TREATMENT OF GASTROINTESTINAL DISORDERS

This application is a 371 of PCT/EP93/00174 filed Jan. 26, 1993.

The present invention relates to novel substituted amidine derivatives, processes for their preparation, pharmaceutical compositions containing them, and their use in therapy, in particular as gastric acid secretion inhibitors.

The present invention, therefore, provides compounds of structure (I):

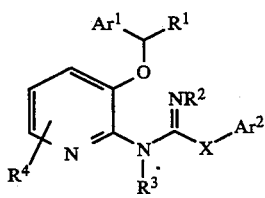

in which:
Ar$^1$ is an optionally substituted phenyl ring;
Ar$^2$ is an optionally substituted phenyl ring;
R$^1$ is hydrogen or C$_{1-4}$alkyl;
R$^2$ is hydrogen or C$_{1-4}$alkyl;
R$^3$ is hydrogen or C$_{1-4}$alkyl;
R$^4$ is hydrogen, halogen, C$_{1-6}$alkyl or C$_{1-6}$alkoxy,
X is CH$_2$ or NR$^5$, and
R$^5$ is hydrogen or C$_{1-4}$alkyl, and the salts thereof.

Suitably, Ar$^1$ is an optionally substituted phenyl ring.

Suitable substituents for the phenyl ring Ar$^1$ include, for example, C$_{1-6}$alkyl, C$_{1-6}$alkoxy, C$_{1-6}$alkylthio, halogen, nitro, cyano, amino, hydroxy, carbamoyl, carboxy, C$_{1-6}$alkanoyl, trifluoromethyl and C$_{1-4}$alkylenedioxy substituents such as methylenedioxy (—OCH$_2$O—). The phenyl rings may be substituted by a single substituent, or up to five substituents as may be synthetically accessible (for example, 2,3,4,5,6-pentafluorophenyl). Preferably, the group Ar$^1$ is unsubstituted phenyl, or phenyl substituted by 1 or more substituents selected from C$_{1-6}$alkyl, C$_{1-6}$alkoxy, C$_{1-6}$alkylthio, halogen, cyano, amino, hydroxy, carbamoyl, carboxy, C$_{1-6}$alkanoyl, trifluoromethyl or by a single substituent in association with a C$_{1-4}$alkylenedioxy. The phenyl ring may be substituted by a single substituent or up to 5 substituents as may be synthetically accessible (for example, 2,3,4,5,6-pentafluorophenyl). More preferably, Ar$^1$ is unsubstituted phenyl, or phenyl substituted by one or two substituents selected from C$_{1-6}$alkyl, C$_{1-6}$alkoxy and halogen. Most preferably Ar$^1$ is unsubstituted phenyl or a phenyl group substituted by a single C$_{1-6}$alkyl or halogen (in particular in the 2-position of the ring), or phenyl substituted by 2 halogen atoms (in particular 2 chlorine or fluorine atoms in the 2- and 6-positions of the ring or a chlorine atom in the 2-position and a fluorine atom in the 6-position of the ring).

Suitably R$^1$ is hydrogen or C$_{1-4}$alkyl; preferably R$^1$ is hydrogen.

Suitably, R$^2$ is hydrogen or C$_{1-4}$alkyl; preferably R$^2$ is hydrogen.

Suitably, R$^3$ is hydrogen or C$_{1-4}$alkyl; preferably R$^3$ is hydrogen.

Suitably, R$^4$ is hydrogen, halogen, C$_{1-6}$alkyl or C$_{1-6}$alkoxy; preferably R$^4$ is hydrogen.

Suitably, Ar$^2$ is an optionally substituted phenyl ring.

Suitable substituents for the phenyl ring Ar$^2$ include, for example, C$_{1-6}$alkyl, C$_{1-6}$alkoxy, C$_{1-6}$alkylthio, halogen, nitro, cyano, amino, hydroxy, carbamoyl, carboxy, C$_{1-6}$alkanoyl, trifluoromethyl and C$_{1-4}$alkylenedioxy substituents such as methylenedioxy (—OCH$_2$O—). The phenyl rings may be substituted by a single substituent, or up to five substituents as may be synthetically accessible.

Preferably, Ar$^2$ is unsubstituted phenyl or phenyl substituted by a single substituent selected from C$_{1-4}$alkyl, C$_{1-4}$alkoxy or halogen. More preferably, Ar$^2$ is unsubstituted phenyl or phenyl substituted by a single halogen atom, in particular chlorine in the 4-position of the ring.

The compounds of the present invention can be prepared by processes analogous to those known to those skilled in the art. In a further aspect, there is, therefore provided a process for preparing compounds of structure (I) and salts thereof, which comprises (a) for compounds in which X is CH$_2$, reaction of a compound of structure (II):

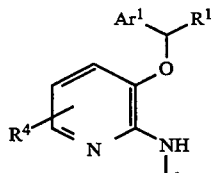

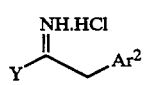

in which Ar$^1$, R$^1$, R$^3$ and R$^4$ are as described for structure (I) with a compound of structure (III) in which Ar$^2$ is as described for structure (I) and Y is a leaving group; (b) for compounds in which X is NR$^5$ and R$^5$ is hydrogen, reaction of a compound of structure (IV)

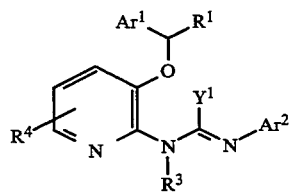

in which Ar$^1$, Ar$^2$ and R$^1$, R$^3$ and R$^4$ are as described for structure (I) and Y$^1$ is a leaving group with an amine of structure H$_2$NR$^2$ in which R$^2$ is as described for structure (I); (c) for compounds in which X is NR$^5$
 (i) reaction of a compound of structure (II) with a compound of structure (V)

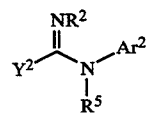

in which Y$^2$ is a leaving group and Ar$^2$, R$^2$ and R$^5$ are as described for structure (I); or
 (ii) reaction of a compound of structure (VI)

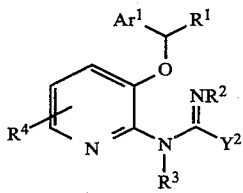

(VI)

in which $R^1$ to $R^4$ and $Ar^1$ are as described for structure (I) and $Y^2$ is a leaving group, with a compound of structure $HNR^5Ar^2$ (VII) in which $R^5$ and $Ar^2$ are as described for structure (I), and optionally thereafter, forming a salt.

Suitable leaving groups Y include for example halide, or $R^6O$ in which $R^6$ is $C_{1-4}$alkyl. Preferably Y is $R^6O$.

Suitable leaving groups $Y^1$ include for example SH activated by mercury as described in the specific examples herein.

Suitable leaving groups $Y^2$ include for example $OR^7$, $SR^7$, halogen or sulphonic acid, in which $R^7$ is $C_{1-4}$alkyl; preferred groups $Y^2$ include $SCH_3$.

The reaction between compounds of structure (II) and compounds of structure (III) can be carried out in a suitable solvent at a temperature of between ambient and the reflux temperature of the solvent used, for as long as it takes for complete reaction to occur. Suitable solvents include, for example, $C_{1-4}$alkanols such as ethanol or methanol. Preferably, the reaction can be carried out in ethanol as a solvent, at reflux temperature.

The reaction between compounds of structure (IV) with an amine $H_2NR^2$ can be carried out in the presence of a suitable solvent such as a $C_{1-4}$alkanol, in particular methanol, at ambient temperature or elevated temperature, until reaction is complete.

The reaction between compounds of structure (II) and (V) can be carried out in the presence of a suitable solvent such as a $C_{1-4}$alkanol such as methanol or ethanol.

The reaction between a compound of structure (VI) and an amine of structure (VII) can be carried out in the presence of a suitable solvent such as a $C_{1-4}$alkanol such as methanol or ethanol.

The intermediate compounds of structures (II) and (III) can be prepared from commercially available starting materials, using standard techniques practised in the art of organic chemistry. For example, compounds of structure (II) can be prepared by reaction of 2-amino-3-hydroxypyridine with the appropriate compound $Ar^1CHR^1X$, in which $Ar^1$ and $R^1$ are as described for structure (I) and X is halogen, in particular bromine, in a suitable solvent, in the presence of a base as hereinafter described. Compounds of structure (III), for example, in which Y is ethoxy, can be prepared by reaction of the appropriate cyano derivative $Ar^2CH_2CN$, in which $Ar^2$ is as described for structure (I), with dry hydrogen chloride gas in ethanol as a reaction solvent.

The compounds of structure (I) and their pharmaceutically acceptable salts exert an anti-secretory effect by inhibition of the gastrointestinal $H^+K^+ATPase$ enzyme (Fellenius, E., Berglindh, T., Sachs, G., Olke, L., Elander, B., Sjostrand, S. E., and Wallmark, B., 1981, Nature, 290, 159-61).

In a further aspect therefore the present invention provides compounds of structure (I) and pharmaceutically acceptable salts thereof for use in therapy. The compounds of structure (I) and their pharmaceutically acceptable salts inhibit exogenously and endogenously stimulated gastric acid secretion and are useful in the treatment of gastrointestinal diseases in mammals, in particular humans.

Such diseases include, for example, gastric and duodenal ulcers, aspiration pneumonitis and Zollinger-Ellison Syndrome.

Further, the compounds of structure (I) can be used in the treatment of other disorders where an anti-secretory effect is desirable for example in patients with gastritis, NSAID induced gastritis, acute upper intestinal bleeding, in patients with a history of chronic and excessive alcohol consumption, and in patients with gastro oesophageal reflux disease (GERD).

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains suitably from 1 to 1000 mg, preferably from 1 to 500 mg (and for parenteral administration contains preferably from 0.1 to 25 rag) of a compound of the formula (I) or a pharmaceutically acceptable salt thereof calculated as the free base.

The present invention also provides a method of inhibiting gastric acid secretion which comprises administering to a mammal in need thereof an effective amount of a compound of the formula (I) or a pharmaceutically acceptable salt thereof; and a method of treatment of diseases of the stomach or intestine based on increased acid secretion which comprises administering to a mammal in need thereof an effective amount of a compound of the formula (I) or a pharmaceutically acceptable salt thereof.

The pharmaceutically acceptable compounds of the invention will normally be administered to a subject for the treatment of gastrointestinal diseases and other conditions caused or exacerbated by gastric acidity. The daily dosage regimen for an adult patient may be, for example, an oral dose of between 1 mg and 1000 mg, preferably between 1 mg and 500 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day.

Suitably the compounds will be administered for a period of continuous therapy, for example for a week or more.

In addition, the compounds of the present invention can be co-administered with further active ingredients, such as antacids (for example magnesium carbonate or hydroxide and aluminium hydroxide), non-steroidal anti-inflammatory drugs (for example indomethacin, aspirin or naproxen), steroids, or nitrite scavengers (for example ascorbic acid or aminosulphonic acid), or other drugs used for treating gastric ulcers (for example histamine H$_2$-antagonists such as cimetidine) or agents having activity against Helicobacter pylori organisms, for example antibiotics such as amoxicillin.

The following examples illustrate the invention. Temperatures are recorded in degrees centigrade.

EXAMPLE 1

N-(3-(Benzyloxy)-2-pyridyl)phenylacetamidine

A mixture of 2-amino-3-benzyloxypyridine (2.5 g, 12.5 mmol) and ethyl phenylacetimidate hydrochloride (2.5 g, 12.5 mmol) in ethanol (100 ml) was heated under reflux for 1 hour. The solvent was evaporated in vacuo, and the residue taken up in chloroform, washed with aqueous sodium bicarbonate, dried and the chloroform evaporated. Treatment with charcoal and recrystallisation from ethyl acetate/petroleum ether gave the product (0.62 g), m.p. 114°–116° C.

C$_{20}$H$_{19}$N$_3$O
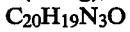
Found C 75.78, H 6.04, N 13.21
Requires C 75.69, H 6.03, N 13.24

EXAMPLE 2

N-(3-(Benzyloxy)-2-pyridyl)-2-methylphenylacetamidine hydrochloride (a) Ethyl 2-methylphenylacetimidate hydrochloride A solution of 2-methylbenzyl cyanide (25 g, 0.19 mol) in absolute ethanol (100 ml) was treated with dry HCl gas with ice cooling for 1 hour. The solvent was evaporated in vacuo, and the residual oil triturated with ether. The solid was filtered off, washed with ether and dried (32.1 g, 95%), then used in subsequent steps without further purification.

(b)
N-(3-(Benzyloxy)-2-pyridyl)-2-methylphenylacetamidine hydrochloride

A mixture of 2-amino-3-benzyloxypyridine (4.0 g, 20 mmol) and ethyl 2-methylphenylacetimidate hydrochloride (4.69 g, 22 mmol) in ethanol (80 ml) was heated under reflux for 1 hour. Evaporation of the solvent gave an oil which was purified by flash chromatography (chloroform/methanol 10:1). The product was obtained as a white crystalline solid (1.2 g), m.p. 119°–120° C.

C$_{21}$H$_{21}$N$_3$O.HCl.0.2H$_2$O
Found C 67.60, H 6.04, N 11.41
Requires C 67.89, H 6.07, N 11.31

EXAMPLE 3

N-(3-(Benzyloxy)-2-pyridyl)-4-methoxyphenylacetamidine hydrochloride (a) Ethyl 4-methoxyphenylacetimidate hydrochloride A solution of 4-methoxyphenylacetonitrile (50 g, 0.34 mol) in absolute ethanol (200 ml) was treated with dry HCl gas with ice cooling for 1 hour. The solvent was evaporated in vacuo, and the residual oil triturated with ether. The solid was filtered off, washed with ether and dried (66 g, 84%), then used in subsequent steps without further purification.

(b)
N-(3-(Benzyloxy)-2-pyridyl)-4-methoxyphenylacetamidine hydrochloride

A mixture of 2-amino-3-benzyloxypyridine (4.0 g, 20 mmol) and ethyl 4-methoxyphenylacetimidate hydrochloride (5.04 g, 22 mmol) in ethanol (80 ml) was heated under reflux for 2 hours. Evaporation of the solvent gave an oil which was purified by flash chromatography (chloroform/methanol) to give the product (1.27 g), m.p. 75°–78° C.

C$_{21}$ H$_{21}$ N$_3$O$_2$.HCl.0.5H$_2$O
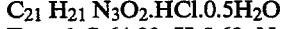
Found C 64.39, H 5.68, N 10.78
Requires C 64.19, H 5.90, N 10.69

EXAMPLE 4

N-(3-(Benzyloxy)-2-pyridyl)-4-fluorophenylacetamidine (a) Ethyl 4-fluorophenylacetimidate hydrochloride A solution of 4-fluorophenylacetonitrile (50 g, 0.37 mol) in absolute ethanol (300 ml) was treated with dry HCl gas with ice cooling for 1 hour. The solvent was evaporated in vacuo, and the residual oil triturated with ether. The solid was filtered off, washed with ether and dried (67 g, 83%), then used in subsequent steps without further purification.

(b)
N-(3-(Benzyloxy)-2-pyridyl)-4-fluorophenylacetamidine

A mixture of 2-amino-3-benzyloxypyridine (4.84 g, 24.2 mmol) and ethyl 4-fluorophenylacetimidate hydrochloride (5.8 g, 26.7 mmol) in ethanol (80 ml) was heated under reflux for 2 hours. Evaporation of the solvent gave an oil which was converted to the free base and purified by flash chromatography (chloroform/methanol) to obtain the product (0.49 g), m.p. 86°–93° C.

C$_{20}$H$_{18}$FN$_3$O.0.5H$_2$O
Found C 69.72, H 5.32, N 12.31, F 55.47

Requires C 69.75, H 5.56, N 12.20, F 55.51

EXAMPLE 5

N-(3-(2-Methylenedioxy)-2-pyridyl)phenylacetamidine hydrochloride (a) 2-Amino-3-(2-methylbenzyloxy)pyridine A mixture of a -bromo-o-xylene (89.6 g, 0.48 mol) and 2-amino-3-hydroxypyridine (48 g, 0.436 mol) in 40% aqueous sodium hydroxide solution (250 ml) and dichloromethane (250 ml) was treated with Adogen 464 (5 ml) and stirred vigorously at room temperature for 16 hours. The aqueous layer was extracted with dichloromethane and the combined organic layers washed with water, dried and evaporated. Chromatography (silica gel, chloroform) gave the product as an oil which later solidified (45.4 g, 49%), m.p. 96°–98° C.

(b) N-(3-(2-Methylbenzyloxy)-2-pyridyl)phenylacetamidine hydrochloride

A mixture of 2-amino-3-(2-methylbenzyloxy)pyridine (5.2 g, 24.2 mmol) and ethyl phenylacetimidate hydrochloride (5.32 g, 26.7 mmol) in ethanol (80 ml) was heated under reflux for 2 hours. Evaporation of the solvent gave an oil which was taken up in chloroform, filtered to remove an insoluble white solid, and purified by flash chromatography (chloroform/methanol) to obtain the product (0.85 g), m.p. 175°–178° C.

$C_{21}H_{21}N_3O.HCl.0.1H_2O$
Found C 67.98, H 6.09, N 11.31
Requires C 68.22, H 6.05, N 11.36

EXAMPLE 6

N-(3-(2-Methylbenzyloxy)-2-pyridyl)-2-methylphenylacetamidine hydrochloride

A mixture of 2-amino-3-(2-methylbenzyloxy)pyridine (5.2 g, 24.2 mmol) and ethyl 2-methylphenylacetimidate hydrochloride (5.7 g, 26.7 mmol) in ethanol (80 ml) was heated under reflux for 2 hours. Evaporation of the solvent gave an oil which was purified by flash chromatography (chloroform/methanol) to obtain the product (1.37 g), m.p. 147°–154° C.

$C_{22}H_{23}N_3O.HCl.0.5H_2O$
Found C 67.61, H 6.39, N 10.74
Requires C 67.59, H 6.45, N 10.74

EXAMPLE 7

N-(3-(2-Methylbenzyloxy)-2-pyridyl)-4-methoxyphenylacetamidine hydrochloride

A mixture of 2-amino-3-(2-methylbenzyloxy)pyridine (5.2 g, 24.2 mmol) and ethyl 4-methoxyphenylacetimidate hydrochloride (6.1 g, 26.7 mmol) in ethanol (80 ml) was heated under reflux for 2 hours, then the solvent evaporated. The residue was taken up in chloroform, filtered to remove an insoluble solid, and the filtrate purified by flash chromatography (chloroform/methanol) to obtain the product (0.29 g), m.p. 58°–67° C.

$C_{22}H_{23}N_3O_2.HCl.0.7H_2O$
Found C 64.36, H 5.98, N 10.19
Requires C 64.36, H 6.23, N 10.23

EXAMPLE 8

N-(3-(2-Methylbenzyloxy)-2-pyridyl)-4-fluorophenylacetamidine hydrochloride

A mixture of 2-amino-3-(2-methylbenzyloxy)pyridine (5.2 g, 24.2 mmol) and ethyl 4-fluorophenylacetimidate hydrochloride (5.8 g, 26.7 mmol) in ethanol (80 ml) was heated under reflux for 2 hours, then the solvent evaporated. The residue was purified by flash chromatography (chloroform/methanol) to obtain the product as a foam (0.49 g), m.p. 59°–64° C.

$C_{21}H_{20}FN_3O.HCl$
Found C 65.32, H 5.46, N 10.99, F 5.36
Requires C 65.37, H 5.49, N 10.89, F 4.92

EXAMPLE 9

N-(3-(4-fluorobenzyloxy)-2-pyridyl)phenylacetamidine hydrochloride (a) 2-Amino-3-(4-fluorobenzyloxy)pyridine A mixture of 4-fluorobenzyl bromide (75 g, 0.396 mol) and 2-amino-3-hydroxypyridine (39.6 g, 0.36 mol) in 40% aqueous sodium hydroxide solution (250 ml) and dichloromethane (250 ml) was treated with Adogen 464 (5 ml) and stirred vigorously at room temperature for 16 hours. The aqueous layer was extracted with dichloromethane and the combined organic layers washed with water, dried and evaporated. Chromatography (silica gel, chloroform) gave the product as an oil which later solidified (45.4 g, 49%), m.p. 96°–98° C.

(b) N-(3-(4-Fluorobenzyloxy)-2-pyridyl)phenylacetamidine hydrochloride

A mixture of 2-amino-3-(4-fluorobenzyloxy)pyridine (5.42 g, 24.2 mmol) and ethyl phenylacetimidate hydrochloride (6.28 g, 26.7 mmol) in ethanol (80 ml) was heated under reflux for 2 hours. Evaporation of the solvent gave an oil which was taken up in chloroform, filtered to remove an insoluble white solid, and purified by flash chromatography (chloroform/methanol) to obtain the product (0.85 g), m.p. 175°–178° C.

$C_{20}H_{18}FN_3O.HCl$
Found C 64.12, H 5.24, N 10.87
Requires C 64.60, H 5.15, N 11.30

EXAMPLE 10

N-(3-(4-Fluorobenzyloxy)-2-pyridyl)-2-methylphenylacetamidine hydrochloride

A mixture of 2-amino-3-(4-fluorobenzyloxy)pyridine (4.36 g, 20 mmol) and ethyl 2methylphenylacetimidate hydrochloride (4.69 g, 22 mmol) in ethanol (80 ml) was heated under reflux for 2 hours. Evaporation of the solvent gave an oil, which was purified by flash chromatography (chloroform/methanol) to obtain the product (1.2 g), m.p. 199°–200° C.

$C_{21}H_{20}FN_3O.HCl$
Found C 65.06, H 5.36, N 10.94
Requires C 65.36, H 5.48, N 10.89

EXAMPLE 11

N-(3-(4-Fluorobenzyloxy)-2-pyridyl)-4-methoxyphenylacetamidine hydrochloride

A mixture of 2-amino-3-(4-fluorobenzyloxy)pyridine (4.36 g, 20 mmol) and ethyl 4-methoxyphenylacetimidate hydrochloride (5.04 g, 22 mmol) in ethanol (80 ml) was heated under reflux for 2 hours. Evaporation of the solvent gave an oil, which was purified by flash chromatography (chloroform/methanol) to obtain the product as a hygroscopic gum (1.2 g), m.p. 199°–200° C.

$C_{21}H_{20}FN_3O_2.HCl.0.4H_2O$
Found C 61.61, H 5.20, N 10.35, F 4.16
Requires C 61.65, H 5.37, N 10.29, F 4.64

EXAMPLE 12

N-(3-(4-Methoxybenzyloxy)-2-pyridyl)phenylacetamidine hydrochloride

(a) 2- Amino- 3-(4-methoxybenzyloxy)pyridine

A mixture of 4-methoxybenzyl bromide (25 g, 0.159 mol) and 2-amino-3-hydroxypyridine (15.9 g, 0.145 mol) in 40% aqueous sodium hydroxide solution (150 ml) and dichloromethane (150 ml) was treated with Adogen 464 (5 ml) and stirred vigorously at room temperature for 16 hours. The mixture was diluted with further water and dichloromethane, the product extracted into dichloromethane, and the combined organic layers washed with water, dried and evaporated. The resulting solid was washed with ether to yield the product (25.6 g, 70%)

(b) N-(3-(4-Methoxybenzyloxy)-2-pyridyl)phenylacetamidine hydrochloride

A mixture of 2-amino-3-(2-methylbenzyloxy)pyridine (4.6 g, 20 mmol) and ethyl phenylacetimidate hydrochloride (4.39 g, 26 mmol) in ethanol (80 ml) was heated under reflux for 2 hours. Evaporation of the solvent gave an oil which was purified by flash chromatography (chloroform/methanol) to obtain the product (0.75 g), m.p. 188°–192° C.

$C_{21}H_{21}N_3O_2.HCl$
Found C 65.72, H 5.78, N 10.89, Cl 9.11
Requires C 65.71, H 5.78, N 10.95, Cl 9.24

EXAMPLE 13

N-(3-(4-Methoxybenzyloxy)-2-pyridyl)-2-methylphenylacetamidine

A mixture of 2-amino-3-(4-methoxybenzyloxy)pyridine (4.6 g, 20 mmol) and ethyl 2methylphenylacetimidate hydrochloride (4.69 g, 22 mmol) in ethanol (80 ml) was heated under reflux for 2 hours. Evaporation of the solvent gave an oil which was taken up in chloroform, convened to the free base by washing with aqueous sodium bicarbonate, and purified by flash chromatography (chloroform/methanol) to obtain the product as a gum (0.38 g).

$C_{22}H_{23}N_3O_2.0.8H_2O$
Found C 70.14, H 6.28, N 11.20
Requires C 70.30, H 6.79, N 11.18

EXAMPLE 14

N-(3-(2,4,6-Trimethylbenzyloxy)-2-pyridyl)-phenylacetamidine hydrochloride

(a) 2-Amino-3-(2,4,6-trimethylbenzyloxy)pyridine

A mixture of 2,4,6-trimethylbenzyl chloride (50 g, 0.296 mol) and 2-amino-3hydroxypyridine (29.6 g, 0.269 mol) in 40% aqueous sodium hydroxide solution (200 ml) and dichloromethane (200 ml) was treated with Adogen 464 (5 ml) and stirred vigorously at room temperature for 16 hours. The product was extracted into dichloromethane and purified by flash chromatography (silica, chloroform) to yield a solid (10.1 g, 14%), m.p. 160°–166° C.

(b) N-(3-(2,4,6-Trimethylbenzyloxy)-2-pyridyl)phenylacetamidine hydrochloride A mixture of 2-amino-3-(2,4,6-trimethylbenzyloxy)pyridine (4.84 g, 20 mmol) and ethyl phenylacetimidate hydrochloride (4.39 g, 22 mmol) in ethanol (80 ml) was heated under reflux for 2 hours. Evaporation of the solvent gave an oil which was purified by flash chromatography (chloroform/methanol) to obtain the product (1.95 g), m.p. 173°–178° C.

$C_{23}H_{25}N_3O.HCl.0.5H_2O$
Found C 68.59, H 6.47, N 10.44, Cl 8.41
Requires C 68.21, H 6.72, N 10.37, Cl 8.75

EXAMPLE 15

N-(3-(2,6-Dichlorobenzyloxy)-2-pyridyl)-phenylacetamidine hydrochloride

(a) 2-Amino-3-(2,6-dichlorobenzyloxy)pyridine

A mixture of 2,6-dichlorobenzyl bromide (50 g, 0.209 mol) and 2-amino-3hydroxypyridine (20.9 g, 0.19 mol) in 40% aqueous sodium hydroxide solution (200 ml) and dichloromethane (200 ml) was treated with Adogen 464 (5 ml) and stirred vigorously at room temperature for 16 hours. A further 200 ml of water was added and the product extracted into dichloromethane, dried, and the solvent evaporated to yield a solid (43.1 g, 76%), m.p. 141°–142° C.

(b) N-(3-(2,6-Dichlorobenzyloxy)-2-pyridyl)phenylacetamidine hydrochloride

A mixture of 2-amino-3-(2,6-dichlorobenzyloxy)pyridine (5.38 g, 20 mmol) and ethyl phenylacetimidate hydrochloride (4.39 g, 22 mmol) in ethanol (80 ml) was heated under reflux for 2 hours. Evaporation of the solvent gave an oil which was purified by flash chromatography (chloroform/methanol) to obtain the product as a hygroscopic foam (1.52 g), m.p. 69°–74° C.

$C_{20}H_{17}Cl_2N_3O.1.1HCl.0.2H_2O$
Found C 55.73, H 4.32, N 9.75, Cl 25.50
Requires C 55.44, H 4.14, N 9.58, Cl 25.76

EXAMPLE 16

N-(3-(2,6-Difluorobenzyloxy)-2-pyridyl)-Phenylacetamidine hydrochloride

(a) 2-Amino-3-(2,6-difluorobenzyloxy)pyridine

A mixture of 2,6-difluorobenzyl bromide (25 g, 0.121 mol) and 2-amino-3hydroxypyridine (12.1 g, 0.11 mol) in 40% aqueous sodium hydroxide solution (200 ml) and dichloromethane (200 ml) was treated with Adogen 464 (5 ml) and stirred vigorously at room temperature for 16 hours. A further 200 ml of water was added and the product extracted into dichloromethane, dried, and the solvent evaporated to yield a solid (18.5 g, 65%), m.p. 124°–128° C.

(b) N-(3-(2,6-Difluorobenzyloxy)-2-pyridyl)phenylacetamidine hydrochloride

A mixture of 2-amino-3-(2,6-difluorobenzyloxy)pyridine (4.72 g, 20 mmol) and ethyl phenylacetimidate hydrochloride (4.39 g, 22 mmol) in ethanol (80 ml) was heated under reflux for 2 hours. Evaporation of the solvent gave an oil which was purified by flash chromatography (chloroform/methanol) to obtain the product as a hygroscopic glass (0.43 g), m.p. 45°–50° C.

$C_{20}H_{17}F_2N_3O.0.8HCl.0.8H_2O$
Found C 60.72, H 4.67, N 10.85, Cl 7.24
Requires C 60.51, H 4.92, N 10.58, Cl 7.15

EXAMPLE 17

N-(3-(2,6-Difluorobenzyloxy)-2-pyridyl)-2-methylphenylacetamidine hydrochloride A mixture of 2-amino-3-(2,6-difluorobenzyloxy)pyridine (4.72 g, 20 mmol) and ethyl 2methylphenylacetimidate hydrochloride (4.69 g, 22 mmol) in ethanol (80 ml) was heated under reflux for 2 hours. Evaporation of the solvent gave art oil which was purified by flash chromatography (chloroform/methanol) to obtain the product (0.18 g), m.p. 127°-135° C.

$C_{21}H_{20}F_2N_3O.HCl$
Found C 62.71, H 4.99, N 10.88, F 9.94
Requires C 62.46, H 4.99, N 10.40, F 9.41

EXAMPLE 18

N-(3-(Pentafluorobenzyloxy)-2-pyridyl)phenylacetamidine hydrochloride (i) 2-Amino-3-(pentafluorobenzyloxy)pyridine.

To a solution of 2-amino-3-hydroxypyridine (8.1 g, 73.6 mmol) in dichloromethane (65 ml) and 40% sodium hydroxide (65 ml) was added Adogen 464 (5 ml) and alpha-bromo-2,3,4,5,6-pentafluorotoluene (20 g, 81 mmol) with vigorous stirring. The mixture was stirred at room temperature for 16 hours and the resulting solid was filtered off, washed and dried to yield the title compound (14 g), m.p.130°-134° C.

(ii) N-(3-(Pentafluorobenzyloxy)-2-pyridyl)phenylacetamidine hydrochloride

2-Amino-3-pentafluorobenzyloxypyridine (11 g, 37.8 mmol) and ethyl phenylacetimidate hydrochloride (9.07 g, 45.4 mmol) in ethanol (350 ml) were heated under reflux for 3 hrs. After evaporation of the solvent, the residue was purified by flash chromatography (silica, 1% methanol/dichloromethane) and trituration with ether to give the title compound (4.0 g), m.p. 189° C.

$C_{20}H_{14}N_3OF_5.HCl$
Found C 54.12, H 3.46, N 9.44
Requires C 54.13, H 3.41, N 9.47

EXAMPLE 19

N-(3-(2-Chloro-4,5-methylenedioxybenzyloxy)-2-pyridyl)phenylacetamidine hydrochloride (i) 2-Amino-3-(2-chloro-4,5-methylenedioxybenzyloxy)pyridine To a solution of 2-amino-3-hydroxypyridine (9.75 g, 0.0886 mol) in dichloromethane (55 ml) and 40% sodium hydroxide (55 ml) was added Adogen 464 (5 ml) and 6-chloropiperonyl chloride (20 g, 0,0975 mol) with vigorous stirring. The mixture was stirred at room temperature for 16 hours. Water (55 ml) was added and the mixture extracted with dichloromethane. The combined organic layers were dried and evaporated, and the residue purified by flash chromatography (silica, 1% methanol/dichloromethane) and trituration with ether to yield the title compound (6 g), m.p. 100°-104° C.

(ii) N-(6-Chloro-4,5-methylenedioxybenzyloxy)-2-pyridyl)phenylacetamidine hydrochloride 2-Amino-3-(6-chloro-4,5-methylenedioxybenzyloxy)pyridine (6 g, 21.6 mmol) and ethyl phenylacetimidate hydrochloride (5.17 g, 26 mmol) in ethanol (150 ml) were heated under reflux for 3 hrs. The solvent was evaporated and the residue purified by flash chromatography (silica, 1% methanol/dichloromethane), trituration with ether and recrystallisation from ethanol to give the tire compound (1.0 g), m.p. 189° C. (softening 170° C.).

$C_{21}H_{18}ClN_3O_3.HCl.0.4H_2O$
Found C 57.44, H 4.55, N 9.66
Requires C 57.38, H 4.54, N 9.56

EXAMPLE 20

N-(3-(2-Chlorobenzyloxy)-2-pyridyl)phenylacetamidine hydrochloride (a) 2-Amino-3-(2-chlorobenzyloxy)pyridine A mixture of 2-chlorobenzyl chloride (47.6 g, 0.296 mol) and 2-amino-3-hydroxypyridine (29.6 g, 0.269 mol) in 40% aqueous sodium hydroxide solution (200 ml) and dichloromethane (200 ml) was treated with Adogen 464 (5 ml) and stirred vigorously at room temperature for 16 hours. A further 200 ml of water was added and the product extracted into dichloromethane, dried, the solvent evaporated and the residue triturated with petroleum ether to obtain the product (32 g, 46%), m.p. 95°-100° C.

(b) N-(3-(2-Chlorobenzyloxy)-2-pyridyl)phenylacetamidine hydrochloride

A mixture of 2-amino-3-(2-chlorobenzyloxy)pyridine (4.69 g, 20 mmol) and ethyl phenylacetimidate hydrochloride (4.39 g, 22 mmol) in ethanol (80 ml) was heated under reflux for 2 hours. Evaporation of the solvent gave an oil which was purified by flash chromatography (chloroform/methanol) to obtain the product (0.97 g), m.p. 149°-155° C.

$C_{20}H_{18}ClN_3O.0.92HCl.0.9H_2O$
Found C 59.95, H 5.03, N 10.51, Cl 16.97
Requires C 59.80, H 5.20, N 10.40, Cl 16.97

EXAMPLE 21

N-(3-(2-Bromobenzyloxy)-2-pyridyl)phenylacetamidine (a) 2-Amino-3-(2-bromobenzyloxy)pyridine A mixture of 2-bromobenzyl bromide (50 g, 0.20 mol) and 2-amino-3-hydroxypyridine (20.0 g, 0.18 mol) in 40% aqueous sodium hydroxide solution (200 ml) and dichloromethane (200 ml) was treated with Adogen 464 (5 ml) and stirred vigorously at room temperature for 16 hours. A further 200 ml of water was added and the product extracted into dichloromethane, dried, and the solvent evaporated to obtain the product (35.4 g, 63%), m.p. 99°-100° C.

(b) N-(3-(2-Bromobenzyloxy)-2-pyridyl)phenylacetamidine

A mixture of 2-amino-3-(2-bromobenzyloxy)pyridine (5.58 g, 20 mmol) and ethyl phenylacetimidate hydrochloride (4.39 g, 22 mmol) in ethanol (80 ml) was heated under reflux for 2 hours. Evaporation of the solvent gave a residue which was purified by chromatography (silica, chloroform/methanol) and recrystallisation from ethanol/ether to obtain the product (0.28 g), m.p. 158°-169° C.

$C_{20}H_{18}BrN_3O.0.9HCl.0.7H_2O$
Found C 54.13, H 4.53, N 9.64, Br 18.46

Requires C 54.38, H 4.63, N 9.51, Br 18.09

EXAMPLE 22

N-(3-(2-Chloro-6-fluorobenzyloxy)-2-pyridyl)-phenylacetamidine hydrochloride (a) 2-Amino-3-(2-chloro-6-fluorobenzyloxy)pyridine A mixture of 2-chloro-6-fluorobenzyl chloride (52.9 g, 0.296 mol) and 2-amino-3hydroxypyridine (29.6 g, 0,269 mol) in 40% aqueous sodium hydroxide solution (200 ml) and dichloromethane (200 ml) was treated with Adogen 464 (5 ml) and stirred vigorously at room temperature for 16 hours. A further 200 ml of water was added and the product extracted into dichloromethane, dried, and the solvent evaporated to obtain the product (46.7 g, 62%), m.p. 123°–130° C.

(b) N-(3-(2-Chloro-6-fluorobenzyloxy)-2-pyridyl)phenylacetamidine hydrochloride

A mixture of 2-amino-3-(2-chloro-6-fluorobenzyloxy)pyridine (5.05 g, 20 mmol) and ethyl phenylacetimidate hydrochloride (4.39 g, 22 mmol) in ethanol (80 ml) was heated under reflux for 2 hours. Evaporation of the solvent gave an oil which was purified by flash chromatography (chloroform/methanol) and recrystallisation from ethanol/ether to obtain the product (1.53 g), m.p. 115°–123° C.

$C_{20}H_{19}ClFN_3O.HCl.0.68H_2O$ 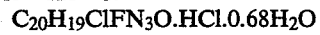
Found C 57.38, H 4.62, N 10.12, Cl 16.85, F 4.34
Requires C 57.40, H 4.66, N 10.04, Cl 16.94, F 4.54

EXAMPLE 23

N-(3-(2-Trifluoromethylbenzyloxy)-2-pyridyl)-phenylacetamidine hydrochloride (a) 2-Amino-3-(2-trifluoromethylbenzyloxy)pyridine A mixture of 2-trifluoromethylbenzyl chloride (50 g, 0.257 mol) and 2-amino-3hydroxypyridine (25.2 g, 0.233 mol) in 40% aqueous sodium hydroxide solution (200 ml) and dichloromethane (200 ml) was treated with Adogen 464 (5 ml) and stirred vigorously at room temperature for 16 hours. A further 200 ml of water was added and the product extracted into dichloromethane, dried, and the solvent evaporated to obtain the product (45.3 g, 66%), m.p. 105°–110° C.

(b) N-(3-(2-Trifluoromethylbenzyloxy)-2-pyridyl)phenylacetamidine hydrochloride

A mixture of 2-amino-3-(2-trifluoromethylbenzyloxy)pyridine (5.36 g, 20 mmol) and ethyl phenylacetimidate hydrochloride (4.39 g, 22 mmol) in ethanol (80 ml) was heated under reflux for 2 hours. Evaporation of the solvent gave an oil which was purified by flash chromatography (chloroform/methanol) and recrystallisation from ethanol/ether to obtain the product (0.41 g), m.p. 105°–112° C.

$C_{21}H_{18}F_3N_3O_2.0.85HCl.2H_2O$ 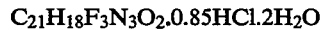
Found C 55.67, H 4.60, N 9.64, Cl 6.53, F 12.79
Requires C 55.60, H 5.06, N 9.26, Cl 6.62, F 12.56

EXAMPLE 24

N-(3-(2-Fluorobenzyloxy)-2-pyridyl)phenylacetamidine hydrochloride (a) 2-Amino-3-(2-fluorobenzyloxy)pyridine A mixture of 2-fluorobenzyl chloride (50 g, 0.346 mol) and 2-amino-3-hydroxypyridine (39 g, 0.3 15 mol) in 40% aqueous sodium hydroxide solution (200 ml) and dichloromethane (200 ml) was treated with Adogen 464 (5 ml) and stirred vigorously at room temperature for 16 hours. A further 200 ml of water was added and the product extracted into dichloromethane, dried, and the solvent evaporated to obtain the product (54.9 g, 80%), m.p. 85°–86° C.

(b) N-(3-(2-Fluorobenzyloxy)-2-pyridyl)phenylacetamidine hydrochloride

A mixture of 2-amino-3-(2-fluorobenzyloxy)pyridine (4.36 g, 20 mmol) and ethyl phenylacetimidate hydrochloride (4.39 g, 22 mmol) in ethanol (80 ml) was heated under reflux for 2 hours. Evaporation of the solvent gave an oil which was purified by flash chromatography (chloroform/methanol) and recrystallisation from ethanol/ether to obtain the product (0.36 g), m.p. 160°–165° C.

$C_{20}H_{18}FN_3O.HCl$ 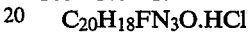
Found C 64.70, H 5.24, N 11.48, Cl 9.26, F 5.13
Requires C 64.60, H 5.15, N 11.30, Cl 9.53, F 5.11

EXAMPLE 25

N-(3-(1-Phenylethoxy)-2-pyridyl)phenylacetamidine hydrochloride (a) 2-Amino-3-(1-phenylethoxy)pyridine A mixture of 1-bromoethylbenzene (55 g, 0.296 mol) and 2-amino-3-hydroxypyridine (29.6 g, 0.269 mol) in 40% aqueous sodium hydroxide solution (200 ml) and dichloromethane (200 ml) was treated with Adogen 464 (10 ml) and stirred vigorously at room temperature for 16 hours. A further 200 ml of water was added and the product extracted into dichloromethane, dried, and the solvent evaporated. Chromatography (silica gel, chloroform-methanol) gave the product as a crystalline solid (37.6 g, 63%), m.p. 79°–83° C.

(b) N-(3-(1-Phenylethoxy)-2-pyridyl)phenylacetamidine hydrochloride

A mixture of 2-amino-3-(1-phenylethoxy)pyridine (4.28 g, 20 mmol) and ethyl phenylacetimidate hydrochloride (4.39 g, 22 mmol) in ethanol (80 ml) was heated under reflux for 2 hours. Evaporation of the solvent gave a residue which was purified by chromatography (silica, chloroform/methanol) to obtain the product (1.05 g), m.p. 75°–80° C.

$C_{21}H_{21}N_3O.0.8HCl.0.5HCl$ 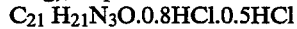
Found C 68.51, H 6.05, N 11.33, Cl 7.66
Requires C 68.24, H 6.21, N 11.37, Cl 7.67

EXAMPLE 26

N-(3-(2,6-Dichlorobenzyloxy)-6-methyl-2-pyridyl)-phenylacetamidine hydrochloride (a) 2-Amino-3-hydroxy-6-methylpyridine 3-Hydroxy-6-methyl-2-nitropyridine (25 g, 0.162 g) was dissolved in ethanol (600 ml) and hydrogenated over 10% palladium-charcoal (3.3 g) at 50 p.s.i. Removal of the catalyst and evaporation of the solvent gave the product (36.4 g, 91%), m.p. 147°–149° C.

(b) 2-Amino-3-(2,6-dichlorobenzyloxy)-6-methylpyridine

A mixture of 2,6-dichlorobenzyl bromide (26.3 g, 0.11 mol) and 2-amino-3-hydroxy-6methylpyridine (12.4 g, 0.1 mol) in 40% aqueous sodium hydroxide solution (200 ml) and dichloromethane (200 ml) was treated with Adogen 464 (10 ml) and stirred vigorously at room temperature for 16 hours. A further 200 ml of water was added and the product extracted into dichloromethane, dried, and the solvent evaporated to obtain the product (21.4 g, 7 6%), m.p. 135°–137° C.

(c)
N-(3-(2,6-Dichlorobenzyloxy)-6-methyl-2-pyridyl)phenyl-acetamidine hydrochloride A mixture of 2-amino-3-(2,6-dichlorobenzyloxy)-6-methyl-pyridine (5.66 g, 20 mmol) and ethyl phenylacetimidate hydrochloride (4.39 g, 22 mmol) in ethanol (80 ml) was heated under reflux for 2 hours. Evaporation of the solvent gave a residue which was purified by chromatography (silica, chloroform/methanol) and recrystallisation from ethanol/ether to obtain the product (1.34 g), m.p. 217°–218° C.
C$_{21}$H$_{19}$Cl$_2$N$_3$O.HCl
Found C 57.71, H 4.63, N 9.61, Cl 23.93
Requires C 57.75, H 4.62, N 9.62, Cl 24.35

EXAMPLE 27

N-(3-(2,6-Difluorobenzyloxy)-6-methyl-2-pyridyl)-phenylacetamidine hydrochloride (a)
2-Amino-3-(2,6-difluorobenzyloxy)-6-methylpyridine A mixture of 2,6-difluorobenzyl bromide (25 g, 0.12 1 mol) and 2-amino-3-hydroxy-6methylpyridine (13.6 g, 0.11 mol) in 40% aqueous sodium hydroxide solution (200 ml) and dichloromethane (200 ml) was treated with Adogen 464 (10 ml) and stirred vigorously at room temperature for 16 hours. A further 200 ml of water was added and the product extracted into dichloromethane, dried, and the solvent evaporated to obtain the product (25.8 g, 94%), m.p. 121°–123° C.

(b)
N-(3-(2,6-Difluorobenzyloxy)-6-methyl-2-pyridyl)phenyl-acetamidine hydrochloride A mixture of 2-amino-3-(2,6-difluorobenzyloxy)-6-methyl-pyridine (5.0 g, 20 mmol) and ethyl phenylacetimidate hydrochloride (4.39 g, 22 mmol) in ethanol (80 ml) was heated under reflux for 2 hours. Evaporation of the solvent gave an oil which was purified by chromatography (silica, chloroform/methanol) and recrystallisation from ethanol/ether to obtain the product (0.56 g), m.p. 173°–177° C.
C$_{21}$H$_{19}$F$_2$N$_3$O.0.96HCl.0.4H$_2$O
Found C 61.54, H 5.00, N 10.34, Cl 8.31, F 9.33
Requires C61.59, H5.10, N 10.26, Cl 8.31, F9.27

EXAMPLE 28

N-(3-(2,4-Dichlorobenzyloxy)-2-pyridyl)-phenylacetamidine hydrochloride (a) 2-Amino-3-(2,4-dichlorobenzyloxy)pyridine A mixture of 2,4-dichlorobenzyl bromide (15 g, 76.7 mmol) and 2-amino-3hydroxypyridine (7.7 g, 69.7 mmol) in 40% aqueous sodium hydroxide solution (52 ml) and dichloromethane (52 ml) was treated with Adogen 464 (5 ml) and stirred vigorously at room temperature for 16 hours. More water was added and the product extracted into dichloromethane, dried, and the solvent evaporated to obtain the product after trituration with ether (13.3 g, 70%), m.p. 120°–121° C.

(b)
N-(3-(2,4-Dichlorobenzyloxy)-2-pyridyl)phenyl-acetamidine hydrochloride

A mixture of 2-amino-3-(2,4-dichlorobenzyloxy)pyridine (5.07 g, 18.8 mmol) and ethyl phenylacetimidate hydrochloride (3.52 g, 25.8 mmol) in ethanol (150 ml) was heated under reflux for 2 hours. Evaporation of the solvent gave an oil which was purified by flash chromatography (dichloromethane/methanol) and trituration with ether to obtain the product (0.59 g), m.p. 185°–187° C.
C$_{20}$H$_{17}$Cl$_2$N$_3$O.HCl
Found C 56.47, H 4.41, N 10.01
Requires C 56.82, H 4.29, N 9.94

EXAMPLE 29

N-(3-(2,5-Dichlorobenzyloxy)-2-pyridyl)-phenylacetamidine hydrochloride (a) 2-Amino- 3-(2,5-dichlorobenzyloxy)pyridine A mixture of 2,5-dichlorobenzyl bromide (14.8 g, 75.9 mmol) and 2-amino-3hydroxypyridine (7.7 g, 69.7 mmol) in 40% aqueous sodium hydroxide solution (52 ml) and dichloromethane (52 ml) was treated with Adogen 464 (5 ml) and stirred vigorously at room temperature for 16 hours. More water was added and the product extracted into dichloromethane, dried, and the solvent evaporated to obtain the product after trituration with ether (8.6 g, 46%), m.p. 103°–104 ° C.

(b)
N-(3-(2,5-Dichlorobenzyloxy)-2-pyridyl)phenyl-acetamidine hydrochloride

A mixture of 2-amino-3-(2,5-dichlorobenzyloxy)pyridine (5.08 g, 18.8 mmol) and ethyl phenylacetimidate hydrochloride (3.52 g, 25.5 mmol) in ethanol (150 ml) was heated under reflux for 2 hours, then evaporated. Flash chromatography (dichloromethane/methanol) and trituration with ether gave the product (0.25 g), m.p. 191°–193° C.
C$_{20}$H$_{17}$Cl$_2$N$_3$O.HCl.0.5H$_2$O
Found C 55.67, H 4.41, N 10.02
Requires C 55.63, H 4.44, N 9.73

EXAMPLE 30

N-(3-Benzyloxy-2-pyridyl)-.N'-phenylguanidine (a) N-(3-Benzyloxy-2-pyridyl)-N'-phenylthiourea A mixture of 2-amino-3-benzyloxypyridine (5.0 g, 25 mmol), phenyl isothiocyanate (3.72 g, 25 mmol) and toluene (20 ml) was heated at reflux for 1.5 hours, then left at room temperature overnight. The solution was diluted with ether, and the product filtered off; yield 5.6 g (67%), m.p. 107°–109° C.

(b) N-(3-Benzyloxy-2-pyridyl)-N'-phenylguanidine

A mixture of N-(3-Benzyloxy-2-pyridyl)-N'-phenylthiourea (1.0 g, 2.9 mmol) and yellow mercuric oxide (1.6 g, 7.4 mmol) was stirred in ethanolic ammonia (20 ml) at room temperature for 18 hours, then heated at reflux for 30 rains. After cooling, the black solid was filtered off and the filtrate evaporated to an oil, which crystallised on trituration with ether/pet. ether. Chromatography (silica, 1-3% methanolic ammonia in dichloromethane) and trituration with pet. ether gave the product (0.49 g, 51%), m.p. 115°–119° C.
C$_{19}$H$_{18}$N$_4$O Found C 71.40, H 5.72, N 17.50
Requires C 71.68, H 5.70, N 17.60

EXAMPLE 31

N-[3-(2-Chloro-6-fluorobenzyloxy)pyrid-2-yl]-2-chlorophenylacetamidine hydrochloride (a) Ethyl 2-chlorophenylacetimidate hydrochloride A solution of 2-chlorobenzyl cyanide (32.4 g, 0.214 mol) in ethanol (70 ml) was cooled to 5 ° C., then HCl gas was passed through with stirring for 30 minutes and the resultant mixture was allowed to stand at room temperature for 18 hours. Evaporation of the solvent and trituration with ether gave the desired product, which was used immediately without further purification. Yield 49.0 g (98%).

(b)
N-[3-(2-Chloro-6-fluorobenzyloxy)pyrid-2-yl]-2-chlorophenylacetamidine hydrochloride A mixture of ethyl 2-chlorophenylacetimidate hydrochloride (5.07 g, 0.0216 mol), 2-amino-3-(2-chloro-6-fluorobenzyloxy)pyridine (4.95 g, 0.0196 mol)and ethanol (150 ml) was heated under reflux for 2 hours. The solvent was evaporated off and the resultant oil was purified by chromatography (silica gel, 1% methanol/-dichloromethane) and trituration with ether. Yield 0.7 g (8%), m.p. 156°–158 ° C.

$C_{20}H_{16}Cl_2FN_3O.HCl.2.1H_2O$
Found C 49.83, H 4.29, N 8.77
Expected C 49.50, H 4.49, N 8.53

EXAMPLE 32

N-(3-Benzyloxy-2-pyridyl)-N'-(4-chlorophenyl)guanidine (a)
N-(3-Benzyloxy-2-pyridyl)-N'-(4-chlorophenyl)thiourea A stirring mixture of 2-amino-3-benzyloxy pyridine (5.37 g, 0.0268 mol) and 4-chlorophenylisothiocyanate (5 g, 0.0295 mol) in toluene (20 ml) was heated under reflux for 2 h. After allowing to cool, the solution was treated with ether, and the resulting solid filtered off, washed and dried. Yield 8.33 g (84%), m.p. 140°–143 ° C.

(b)
N-(3-Benzyloxy-2-pyridyl)-N'-(4-chlorophenyl)guanidine

To a stirring suspension of N-(3-benzyloxy-2-pyridyl)-N'-(4-chlorophenyl)thiourea (1.5 g, 0.00406 mol) in ammonia-saturated methanol (30 ml) was added yellow mercuric oxide (2.2 g, 0.01 mol). Stirring was continued for 20 h, then the solvent evaporated and the black residue treated with chloroform and filtered through celite. The filtrate was evaporated to a whim solid, which was recrystallised from ethyl acetam. Yield 0.76 g (53%), m.p. 170°–172 ° C.

$C_{19}H_{17}ClN_4O$
Found C 64.97, H 4.89, N 16.04
Expected C 64.68, H 4.86, N 15.88

EXAMPLE 33

N-(3-Benzyloxy-2-pyridyl)-N'-(4-cyanophenyl)guanidine (a)
N-(3-Benzyloxy-2-pyridyl)-N'-(4-cyanophenyl)thiourea A stirring mixture of 2-amino-3-benzyloxy pyridine (5.68 g, 0.0284 mol) and 4cyanophenyl isothiocyanate (5 g, 0.0312 mol) in toluene (20 ml) was heated under reflux for 2 h. After allowing to cool, the solution was treated with ether, and the resulting solid filtered off, washed and dried. Yield 9.4 g (92%), m.p. 163°–165 ° C.

(b)
N-(3-Benzyloxy-2-pyridyl)-N'-(4-cyanophenyl)guanidine

To a stirring suspension of N-(3-benzyloxy-2-pyridyl)-N'-(4-cyanophenyl)thiourea (2 g, 0.0055 mol) in ammonia-saturated methanol (40 ml) was added yellow mercuric oxide (3 g, 0.014 mol). Stirring was continued for 20 h, then the mixture filtered through celite, and the solid washed several times with chloroform. The filtrate was evaporated to a white solid, which was triturated with ether. Yield 1.12 g (59%), m.p. 173°–175 ° C.

$C_{20}H_{17}N_5O$
Found C 69.79, H 4.94, N 20.44
Expected C 69.96, H 4.99, N 20.39

EXAMPLE 34

N-(3-Benzyloxypyrid-2-yl)-N'-(4-trifluoromethylphenyl)guanidine (a)
N-(3-Benzyloxypyrid-2-yl)-N'-(4-trifluoromethylphenyl)thiourea A mixture of 2-amino-3-benzyloxypyridine (2.34 g, 0.0117 mol), 4-trifluoromethylphenyl isothiocyanate (2.85 g, 0.014 mol) and toluene (10 ml) was refluxed for 3.5 hours, then cooled and treated with ether to induce crystallisation of the product. Yield 3.06 g (65%), m.p. 165°–167 ° C.

(b)
N-(3-Benzyloxypyrid-2-yl)-N'-(4-trifluoromethylphenyl)guanidine

A mixture of N-(3-benzyloxypyrid-2-yl)-N'-(4-trifluoromethylphenyl)thiourea (3.08 g, 0.0076 mol), yellow mercuric oxide (2 g, 0.0092 mol) and methanolic ammonia solution (40 ml) was stirred for 48 hours at room temperature, then the solvent was removed in vacuo and the residue extracted with boiling chloroform and filtered hot. Evaporation of the filtrate and recrystallisation from acetonitrile gave the desired product. Yield 2.05 g (70%), m.p. 154°–155 ° C.

$C_{20}H_{17}F_3N_4O$
Found C 62.18, H 4.61, N 14.56
Expected C 62.17, H 4.43, N 14.50

EXAMPLE 35

N-(3-Benzyloxy)pyrid-2-yl-N'-(3,4-dichlorophenyl)-guanidine (a)

N-(3-Benzyloxypyrid-2-yl)-N'-(3,4-dichlorophenyl)thiourea

A mixture of 2-amino-3-benzyloxypyridine (2.14 g, 0.011 mol), 3,4-dichlorophenyl isothiocyanate (2.62 g, 0.013 mol) and toluene (10 ml) was refluxed for 3.5 hours, then cooled and treated with ether to induce crystallisation of the product. Yield 3.64 g (84%), m.p. 144°–146° C.

(b)

N-(3-Benzyloxypyrid-2-yl)-N'-(3,4-dichlorophenyl)-guanidine

A mixture of N-(3-benzyloxypyrid-2-yl)-N'-(3,4-dichlorophenyl)thiourea (3.59 g, 0.009 mol), yellow mercuric oxide (2.34 g, 0.011 mol) and methanolic ammonia (40 ml) was stirred for 2 days at room temperature. The solvent was removed in vacuo and the black residue was boiled with chloroform and filtered hot. Evaporation of the solvent and recrystallisation from acetonitrile gave the desired product. Yield 2.44 g (70%), m.p. 161°–162° C.

$C_{19}H_{16}Cl_2N_4O$ 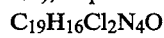
Found C 58.61, H 4.25, N 14.34
Expected C 58.93, H 4.16, N 14.47

EXAMPLE 36

N-[3-(2-Methylbenzyloxy)pyrid-2-yl]-N'-phenylguanidine (a)

N-[3-(2-Methylbenzyloxy)pyrid-2-yl]-N'-phenylthiourea

A mixture of 2-amino-3-(2-methylbenzyloxy)pyridine (1.67 g, 0.0078 mol), phenyl isothiocyanate (1.26 g, 0.0093 mol) and toluene (10 ml) was refluxed for 3.5 hours, then cooled and treated with ether to induce crystallisation of the product. Yield 1.8 g (66%), m.p. 150°–151° C.

(b)

N-[3-(2-Methylbenzyloxy)pyrid-2-yl]-N'-phenylguanidine

A mixture of N-[3-(2-methylbenzyloxy)pyrid-2-yl]-N'-phenylthiourea (1.76 g, 0.005 mol), yellow mercuric oxide (1.31 g, 0.006 mol) and methanolic ammonia (40 ml) was stirred for 3 days at room temperature. The solvent was removed in vacuo and the black residue was boiled with chloroform and filtered hot. Evaporation of the solvent and recrystallisation from acetonitrile gave the desired product. Yield 1.2 g (72%), m.p. 157°–158° C.

$C_{20}H_{20}N_4O$ 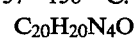
Found C 72.29, H 6.11, N 16.85
Expected C 72.27, H 6.06, N 16.85

EXAMPLE 37

N-[3-(2-Methylbenzyloxy)pyrid-2-yl]-N'-(4-chlorophenyl)guanidine (a)

N-[3-(2-Methylbenzyloxy)pyrid-2-yl]-N'-(4-chlorophenyl)thiourea

A mixture of 2-amino-3-(2-methylbenzyloxy)pyridine (1.19 g, 0.0056 mol), 4-chlorophenyl isothiocyanate (1.15 g, 0.0068 mol) and toluene (10 ml) was refluxed for 2.5 hours, then cooled and treated with ether to induce crystallisation of the product. Yield 1.63 g (77%), m.p. 181°–183° C.

(b)

N-[3-(2-Methylbenzyloxy)pyrid-2-yl]-N'-(4-chlorophenyl)guanidine

A mixture of N-[3-(2-methylbenzyloxy)pyrid-2-yl]-N'-(4-chlorophenyl)thiourea (0.99 g, 0.0026 mol), yellow mercuric oxide (0.67 g, 0.003 mol) and methanolic ammonia solution (40 ml) was stirred at room temperature for 48 hours. The solvent was removed in vacuo and the black residue was boiled with chloroform and filtered hot. Evaporation of the solvent and recrystallisation from acetonitrile gave the desired product. Yield 0.59 g (62%), m.p. 158°–159° C.

$C_{20}H_{19}ClN_4O$ 
Found C 65.46, H 5.26, N 15.34
Expected C 65.48, H 5.22, N 15.27

EXAMPLE 38

N-[3-(2-Fluorobenzyl)pyrid-2-yl]-N'-(4-chlorophenyl)-guanidine (a)

N-[3-(2-Fluorobenzyloxy)pyrid-2-yl]-N'-(4-chlorophenyl)thiourea

A mixture of 2-amino-3-(2-fluorobenzyloxy)pyridine (1.98 g, 0.0091 mol), 4chlorophenyl isothiocyanate (1.83 g, 0.011 mol) and toluene (10 ml) was refluxed for 3.5 hours, cooled and treated with diethyl ether to induce crystallisation of the product. Yield 1.98 g (56%), m.p. 141°–143

(b)

N-[3-(2-Fluorobenzyl)pyrid-2-yl]-N'-(4-chlorophenyl)-guanidine

A mixture of yellow mercuric oxide (1.35 g, 0.0062 mol), N-[3-(2-fluorobenzyloxy)pyrid2-yl]-N'-(4-chlorophenyl)thiourea (1.98 g, 0.005 1 mol) and methanolic ammonia solution (40 ml) was stirred for 2 days at room temperature. The solvent was removed in vacuo and the black residue was boiled with chloroform and filtered hot. Evaporation of the solvent and recrystallisation from acetonitrile gave the desired product. Yield 0.34 g (18%), m.p. 175°–176° C.

$C_{19}H_{16}ClFN_4O$ 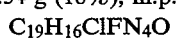
Found C 61.30, H 4.48, N 14.99
Expected C 61.54, H 4.35, N 15.11

EXAMPLE 39

N-[3-(2-Chlorobenzyloxy)pyrid-2-yl]-N'-(4-chlorophenyl)guanidine (a)

N-[3-(2-Chlorobenzyloxy)pyrid-2-yl]-N'-(4-chlorophenyl)thiourea

A mixture of 2-amino-3-(2-chlorobenzyloxy)pyridine (1.81 g, 0.0077 mol), 4chlorophenyl isothiocyanate (1.59 g, 0.0094 mol) and toluene (10 ml) was refluxed for 2.5 hours, cooled and treated with diethyl ether to induce crystallisation of the product. Yield 2.54 g (90%), m.p. 177° 179 ° C.

(b)

N-[3-(2-Chlorobenzyloxy)pyrid-2-yl]-N'-(4-chlorophenyl)guanidine

A mixture of yellow mercuric oxide (1.06 g, 0.0049 mol), N-[3-(2-chlorobenzyloxy)pyrid2-yl]-N'-(4-chlorophenyl)thiourea (1.56 g, 0,004 mol) and methanolic ammonia solution (40 ml) was stirred for 2 days at room temperature. The solvent was removed in vacuo and the black residue was boiled with chloroform and filtered hot. Evaporation of the solvent and recrystallisation from acetonitrile gave the desired product. Yield 0.72 g, (46%),m.p. 162°–163 ° C.

$C_{19}H_{16}Cl_2N_4O$
Found C 58.78, H 4.31, N 14.47
Expected C 58.93, H 4.16, N 14.47

EXAMPLE 40

N-[3-(4-Methylbenzyloxy)pyrid-2-yl]-N'-(4-chlorophenyl)guanidine a) 2-Amino-3-(4-methylbenzyloxy)pyridine A mixture of 2-amino-3-hydroxypyridine (2.7 g, 0.024 mol), dichloromethane (40 ml) and 40% aqueous sodium hydroxide solution (40 ml) was stirred for 5 rains, then 4methylbenzyl bromide (4.51 g, 0.024 mol) and Adogen 464 (3 ml) were added and stirring was continued for 16 hours. The mixture was diluted with water and extracted with dichloromethane (×2), and the combined organic layers dried, evaporated, and triturated with ether. Yield 2.92 g (56%), m.p. 123° 125 ° C.

(b)

N-[3-(4-Methylbenzyloxy)pyrid-2-yl]-N'-(4-chlorophenyl)thiourea

A mixture of 2-amino-3-(4-methylbenzyloxy)pyridine (1.45 g, 0.0068 mol), 4chlorophenyl isothiocyanate (1.38 g, 0.008 mol) and toluene (10 ml) was refluxed for 3.5 hours, then cooled and treated with diethyl ether to induce crystallisation of the product. Yield 1.8 g (70%), m.p. 145°–147 ° C.

(c)

N-[3-(4-Methylbenzyloxy)pyrid-2-yl]-N'-(4-chlorophenyl)guanidine

A mixture of yellow mercuric oxide (0.68 g, 0.0031 mol), N-[3-(4-methylbenzyloxy)pyrid-2-yl]-N'-(4-chlorophenyl)thiourea (1.01 g, 0.0026 mol) and methanolic ammonia solution (40 ml) was stirred for 2 days at room temperature. The solvent was removed in vacuo and the black residue was boiled with chloroform and filtered hot. Evaporation of the solvent and recrystallisation from acetonitrile gave the desired product. Yield 0.5 g (52%), m.p. 174°–175 ° C.

$C_{20}H_{19}ClN_4O$
Found C 65.11, H 5.27, N 15.18
Expected C 65.48, H 5.22, N 15.27

EXAMPLE 41

N-[3-(4-Methoxybenzyloxy)pyrid-2-yl]-N'-phenylguanidine (a)

N-[3-(4-Methoxybenzyloxy)pyrid-2-yl]-N'-phenylthiourea

A mixture of 2-amino-3-(4-methoxybenzyloxy)pyridine (1.91 g, 0.0083 mol), phenyl isothiocyanate (1.4 g, 0.01 mol) and toluene (10 ml) was refluxed for 3.5 hours, then cooled and treated with diethyl ether to induce crystallisation of the product. Yield 2.18 g (72%), m.p. 123°–125 ° C.

(b)

N-[3-(4-Methoxybenzyloxy)pyrid-2-yl]-N'-phenylguanidine

A mixture of yellow mercuric oxide (1.51 g, 0.0069 mol), N-[3-(4-methoxybenzyloxy)pyrid-2-yl]-N'-phenylthiourea (2.14 g, 0.0058 mol) and methanolic ammonia solution (40 ml) was stirred for 2 days at room temperature. The solvent was removed in vacuo and the black residue was boiled with chloroform and filtered hot. Evaporation of the solvent followed by trituration with ether and recrystallisation from acetonitrile gave the desired product. Yield 1.27 g (62%), m.p. 141°–143 ° C.

$C_{20}H_{20}N_4O_2$
Found C 69.31, H 5.91, N 16.10
Expected C 68.95, H 5.79, N 16.08

EXAMPLE 42

N-(3-(4-Methoxybenzyloxy)pyrid-2-yl)-N'-(4-chlorophenyl)-guanidine (a)

N-(3-(4-Methoxybenzyloxy)pyrid-2-yl)-N'-(4-chlorophenyl)thiourea

A mixture of 2-amino-3-(4-methoxybenzyloxy)pyridine (1.80 g, 0.0078 mol), 4chlorophenyl isothiocyanate (1.58 g, 0.0094 mol) and toluene (10 ml) was refluxed for 3.5 hours, then cooled and treated with diethyl ether to induce crystallisation of the product. Yield 2.2 g (70.5%), m.p. 136°–138 ° C.

(b)

N-(3-(4-Methoxybenzyloxy)pyrid-2-yl)-N'-(4-chlorophenyl)guanidine

A mixture of yellow mercuric oxide (1.05 g, 0.00488 mol), N-[3-(4-methoxybenzyloxy)pyrid-2-yl]-N'-(4-chlorophenyl)thiourea (1.5 g, 0.0041 mol)and methanolic ammonia solution (40 ml) was stirred for 2 days at room temperature. The solvent was removed in vacuo and the black residue was boiled with chloroform and filtered hot. Evaporation of the solvent followed by trituration with ether and recrystallisation from acetonitrile gave the desired product. Yield 0.96 g (61.5%) m.p. 165°–166 ° C.

$C_{20}H_{19}ClN_4O_2$
Found C 63.03, H 5.10, N 14.65, Cl 9.20
Expected C 62.75, H 5.00, N 14.63, C; 9.26

EXAMPLE 43

N-[3-(4-Chlorobenzyloxy)pyrid-2-yl]-N'-phenylguanidine (a) 2-Amino-3-(4-chlorobenzyloxy)pyridine A mixture of 2-amino-3-hydroxy pyridine (3.45 g, 0.313 mol), dichloromethane (20 ml) and 40% aqueous sodium hydroxide solution (20 ml) was stirred for five minutes, then 2chlorobenzyl bromide (6.09 g, 0.0315 mol) and Adogen 464 (3 ml) were added and stirring continued for 16 hours. The mixture was diluted with water and extracted with dichloromethane. Drying and evaporation of the organic extracts, and trituration with ether gave the desired product. Yield 3.5 g (48%), m.p. 121°–123 ° C.

(b) N-[3-(4-Chlorobenzyloxy)pyrid-2-yl]-N'-phenylthiourea

A mixture of 2-amino-3-(4-chlorobenzyloxy)pyridine (3.37 g, 0,014 mol), phenyl isothiocyanate (2.33 g, 0,017 mol) and toluene (10 ml) was refluxed for 3.5 hours, then cooled and treated with diethyl ether to induce crystallisation of the product. Yield 4.36 g (82%), m.p. 162°–164 ° C.

(c) N-[3-(4-Chlorobenzyloxy)pyrid-2-yl]-N'-phenylguanidine

A mixture of N-[3-(4-chlorobenzyloxy)pyrid-2-yl]-N'-phenylthiourea (3.00 g, 0.008 mol), yellow mercuric oxide (2.17g, 0.01 mol) and methanolic ammonia solution (40 ml) was stirred for 48 hours. The solvent was removed in vacuo and the black residue was boiled with chloroform and filtered hot. Evaporation of the solvent and recrystallisation from acetonitrile gave the desired product. Yield 1.8 g (63%), m.p. 173°–174 ° C.

$C_{19}H_{17}ClN_4O$
Found C 64.39, H 5.00, N 15.92
Expected C 64.68, H 4.86, N 15.88

EXAMPLE 44

N-[3-(2-Fluoro-6-chlorobenzyloxy)pyrid-2-yl]-N'-phenylguanidine (a) N-[3-(2-Fluoro-6-chlorobenzyloxy)pyrid-2-yl]-N'-phenylthiourea A mixture of 2-amino-3-(2-fluoro-6-chlorobenzyloxy)pyridine (7.6 g, 0.03 mol), phenyl isothiocyanate (3.95 ml, 0.033 mol) and toluene (25 ml) was refluxed for 2.5 hours, then cooled and treated with diethyl ether to induce crystallisation of the product. Yield 8.47 g (73%), m.p. 143°–145 ° C.

(b) N-[3-(2-Fluoro-6-chlorobenzyloxy)pyrid-2-yl]-N'-phenylguanidine

A mixture of N-[3-(2-fluoro-6-chlorobenzyloxy)pyrid-2-yl]-N'-phenylthiourea (2 g, 0.0052 mol), yellow mercuric oxide (1.34g, 0.0062 mol) and methanolic ammonia solution (40 ml) was stirred for 72 hours. The solvent was removed in vacuo and the black residue was treated with chloroform and filtered through celite. Evaporation of the solvent and recrystallisation from acetonitrile gave the desired product. Yield 1.07 g (56%), m.p. 147°–149 ° C.

$C_{19}H_{16}ClFN_4O$
Found C 61.51, H 4.39, N 15.15
Expected C 61.54, H 4.35, N 15.11

EXAMPLE 45

N-[3-(2-Fluoro-6-chlorobenzyloxy)pyrid-2-yl]-N'-(4-chlorophenyl)guanidine (a) N-[3-(2-Fluoro-6-chlorobenzyloxy)pyrid-2-yl]-N'-(4-chlorophenyl)thiourea A mixture of 2-amino-3-(2-fluoro-6-chlorobenzyloxy)pyridine (3.46 g, 0.014 mol), 4chlorophenyl isothiocyanate (2.55 g, 0.015 mol) and toluene (10 ml) was refluxed for 2 hours, then cooled and treated with diethyl ether to induce crystallisation of the product. Yield 4.64 g (73%), m.p. 162°–164 ° C.

(b) N-[3-(2-Fluoro-6-chlorobenzyloxy)pyrid-2-yl]-N'-(4-chlorophenyl)guanidine

A mixture of N-[3-(2-fluoro-6-chlorobenzyloxy)pyrid-2-yl]-N'-(4-chlorophenyl)thiourea (2 g, 0.0047 mol), yellow mercuric oxide (2.56 g, 0.012 mol) and methanolic ammonia solution (40 ml) was stirred for 40 hours. The solvent was removed in vacuo and the black residue was treated with chloroform and filtered through celite. Evaporation of the solvent and recrystallisation from chloroform/ether gave the desired product. Yield 0.96 g (50%), m.p. 168°–170 ° C.

$C_{19}H_{15}Cl_2FN_4O$
Found C 56.30, H 3.79, N 13.84
Expected C 56.31, H 3.73, N 13.82

EXAMPLE 46

N-[3-(2-Chloro-6-fluorobenzyloxy)pyrid-2-yl]-N'-(2-fluorophenyl)guanidine (a) N-[3-(2-Chloro-6-fluorobenzyloxy)pyrid-2-yl]-N'-(2-fluorophenyl)thiourea A mixture of 2-amino-3-(2-chloro-6-fluorobenzyloxy)pyridine (7.48g, 0.03 mol), 2fluorophenyl isothiocyanate (5.0 g, 0.033 mol) and toluene (30 ml) was heated under reflux for 1.5 hours, then cooled and diluted with ether to induce crystallisation of the product. Yield 7.9 g (59 %), m.p. 145°–147 ° C.

(b) N-[3-(2-Chloro-6-fluorobenzyloxy)pyrid-2-yl]-N'-(2-fluorophenyl)guanidine

A mixture of yellow mercuric oxide (4.13g, 0.019 mol), N-[3-(2-chloro-6-fluoro -benzyloxy)pyrid-2-yl]-N'-(2-fluorophenyl)thiourea (3.10g, 0.0076 mol) and methanolic ammonia solution (60 ml) was stirred for 24 hours at room temperature. The mixture was filtered through celite and the filtrate evaporated to a yellow solid, which was recrystallised from ethyl acetate/pet. ether. Yield 1.51 g (51%), m.p 138°–140 ° C.

$C_{19}H_{15}ClF_2N_4O$
Found C 58.73, H 3.91, N 14.40
Expected C 58.69, H 3.89, N 14.41

EXAMPLE 47

N-[3-(2-Chloro-6 fluorobenzyloxy)pyrid-2-yl]-N'-(4-nitrophenyl)guanidine (a) N-[3-(2-Chloro-6 fluorobenzyloxy)pyrid-2-yl]-N'-(4-nitrophenyl)thiourea A mixture of 2-amino-3-(2-chloro-6-fluorobenzyloxy)pyridine (7.01g, 0.028 mol), 4nitrophenyl isothiocyanate (5.31g, 0.03 mol) and toluene (50 ml) was heated under reflux for 2 hours, then cooled and treated with ether to induce crystallisation of the product. Yield 11.07 g (86%), m.p. 214° 215 ° C.

(b) N-[3-(2-Chloro-6 fluorobenzyloxy)pyrid-2-yl]-N'-(4-nitrophenyl)guanidine

A mixture of yellow mercuric oxide (1.26g, 0.006 mol), N-[3-(2-chloro-6 fluorobenzyloxy)pyrid-2-yl]-N'-(4-nitrophenyl)thiourea (2.08g, 0.005 mol) and methanolic ammonia solution (40 ml) was stirred for 24 hours at room temperature, then heated under reflux for 30 min. The solvent was removed in vacuo and the black residue was boiled with chloroform and filtered hot. Evaporation of the solvent and recrystallisation from ethanol gave the desired product. Yield 1.16 g (58%), m.p 180°-182 ° C.

$C_{19}H_{15}ClFN_5O_3$

Found C 54.84, H 3.71, N 16.83

Expected C 54.88, H 3.64, N 16.84

EXAMPLE 48

N-[3-(2-Chloro-6-fluorobenzyloxy)pyrid-2-yl]-N'-(4-methylphenyl)guanidine (a) N-[3-(2-Chloro-6-fluorobenzyloxy)pyrid-2-yl]-N'-(4-methylphenyl)thiourea A mixture of 2-amino-3-(2-chloro-6-fluorobenzyloxy)pyridine (2g, 0.008 mol), 4methylphenyl isothiocyanate (1.43g, 0.0096 mol) and toluene (10 ml) was heated under reflux for 5 hours, then cooled and diluted with ether to induce crystallisation of the product. Yield 2.61g (82%) m.p. 138°-140 ° C.

(b) N-[3-(2-Chloro-6-fluorobenzyloxy)pyrid-2-yl]-N'-(4-methylphenyl)guanidine

A mixture of yellow mercuric oxide (0.65g, 0.0025 mol), N-[3-(2-chloro-6-fluorobenzyloxy)pyrid-2-yl]-N'-4-methylphenylthiourea (1 .0g, 0.0025 mol) and methanolic ammonia solution (30 ml) was stirred for 3 days at room temperature. The solvent was removed in vacuo and the black residue was boiled with chloroform and filtered hot. Evaporation of the solvent followed by recrystallisation from ethanol gave the desired product. Yield 0.55 g, (57%), m.p. 136°-138 ° C.

$C_{20}H_{18}N_4ClFO$

Expected C 62.42, H 4.71, N 14.56

Found C 62.57, H 4.81, N 14.66

EXAMPLE 49

N-[3-(2-Chloro-6-fluorobenzyloxy)pyrid-2-yl]-N'-(4-fluorophenyl)guanidine (a)

N-[3-(2-Chloro-6-fluorobenzyloxy)pyrid-2-yl]-N'-(4-fluorophenyl)thiourea

A mixture of 2-amino-3-(2-chloro-6-fluorobenzyloxy)pyridine (2g, 0.008 mol), 4fluorophenyl isothiocyanate (1.45g, 0.0096 mol) and toluene (10 ml) was heated under reflux for 5 hours, then cooled and diluted with ether to induce crystallisation of the product. Yield 2.31 g (71%), m.p. 146°-148 ° C.

(b)

N-[3-(2-Chloro-6-fluorobenzyloxy)pyrid-2-yl]-N'-(4-fluorophenyl)guanidine

A mixture of yellow menzuric oxide (0.65g, 0.003 mol), N-[3-(2-chloro-6-fluorobenzyloxy)pyrid-2-yl]-N'-4-fluorophenylthiourea (1 .0g, 0.0025 mol) and methanolic ammonia solution (30 ml) was stirred for 3 days at room temperature. The solvent was removed in vacuo and the black residue was boiled with chloroform and filtered hot. Evaporation of the solvent followed by recrystallisation from ethanol gave the desired product. Yield 0.38 g, (40%), m.p. 152°-154 ° C.

$C_{19}H_{15}ClF_2N_4O$

Expected C58.69, H3.89, N 14.41, Cl 9.12

Found C 58.62, H 4.05, N 14.49, Cl 9.14

EXAMPLE 50

N-[3-(2-Chloro-6-fluorobenzyloxy)pyrid-2-yl]-N'-(2-methyl-4 chlorophenyl)guanidine (a)- N-[3-(2-Chloro-6-fluorobenzyloxy)pyrid-2-yl]-N'-(2-methyl-4chlorophenyl)thiourea A mixture of 2-amino-3-(2-chloro-6-fluorobenzyloxy)pyridine (2 g, 0.008 mol), (2-methyl-4-chlorophenyl isothiocyanate (1.76 g, 0.0096 mol) and toluene (10 ml) was heated under reflux for 5 hours, then cooled and diluted with ether to induce crystallisation of the product. Yield 2.72g (77%), m.p. 176°-177 ° C.

(b)

N-[3-(2-Chloro-6-fluorobenzyloxy)pyrid-2-yl]-N'-(2-methyl-4chlorophenyl)guanidine A mixture of yellow mercuric oxide (0.6 g, 0.0028 mol), N-[3-(2-chloro-6-fluorobenzyloxy)pyrid-2-yl]-N'-2-methyl-4-chlorophenylthiourea (1.0 g, 0.0023 mol) and methanolic ammonia solution (30 ml) was stirred for 3 days at room temperature. The solvent was removed in vacuo and the black residue was boiled with chloroform and filtered hot. Evaporation of the solvent followed by recrystallisation from ethanol gave the desired product. Yield 0.63 g (65%), m.p. 155°-156 ° C.

$C_{20}H_{17}Cl_2FN_4O$

Expected C 57.29, H 4.09, N 13.36, Cl 16.91

Found C 57.42, H 4.20, N 13.53, Cl 17.33

EXAMPLE 51

N-[3-(2,6-Dichlorobenzyloxy)pyrid-2-yl]-N'-phenylguanidine

(a)
N-[3-(2,6-Dichlorobenzyloxy)pyrid-2-yl]-N'-phenylthiourea

A mixture of 2-amino-3-(2,6-dichlorobenzyloxy)pyridine (2 g, 0.007 1 mol), phenyl isothiocyanate (1.15 g, 0.0085 mol) and toluene (10 ml) was heated under reflux for 1.5 hours, then cooled and diluted with ether to induce crystallisation of the product, which was recrystallised from ethanol/ether. Yield 1.2 g (42%), m.p. 148°–149 °C.

(b)
N-[3-(2,6-Dichlorobenzyloxy)pyrid-2-yl]-N'-phenylguanidine

A mixture of yellow mercuric oxide (0.62 g, 0.0029 mol), N-[3-(2-,6-dichlorobenzyloxy)pyrid-2-yl]-N'-phenylthiourea (1.0 g, 0.0025 mol) and methanolic ammonia solution (30 ml) was stirred for 15 hours at room temperature. The solvent was removed in vacuo and the black residue was boiled with chloroform and filtered hot. Evaporation of the solvent followed by recrystallisation from ethanol gave the desired product. Yield 0.33 g (55%), m.p. 163°–165 °C.

$C_{19}H_{16}Cl_2N_4O$ 

Expected C 58.93, H 4.16, N 14.47, Cl 18.31

Found C 58.96, H 4.35, N 14.39, Cl 18.40

EXAMPLE 52

N-(3-(2,6-Dichlorobenzyloxy)-pyrid-2-yl)-N'-(4-chlorophenyl)guanidine

(a)
N-(3-(2,6-Dichlorobenzyloxy)-pyrid-2-yl)-N'-(4-chlorophenyl)thiourea

A mixture of 2-amino-3-(2,6-dichlorobenzyloxy)pyridine (5 g, 0.018 mol), 4-chlorophenyl isothiocyanate (3.76 g, 0.022 mol) and toluene (20 ml) was heated under reflux for 3 hours, then cooled and diluted with ether to induce crystallisation of the product, which was recrystallised from ethanol/ether. Yield 6.69 g (82%), m.p. 179°–180 °C.

(b)
N-(3-(2,6-Dichlorobenzyloxy)-pyrid-2-yl)-N'-(4-chlorophenyl)guanidine

A mixture of yellow mercuric oxide (1.18g, 0.0054mol), N-[3-(2-,6-dichlorobenzyloxy)pyrid-2-yl]-N'-4-chlorophenylthiourea (2.0g, 0.0045mol) and methanolic ammonia solution (40 ml) was stirred for 5 days at room temperature. The solvent was removed in vacuo and the black residue was boiled with chloroform and filtered hot. Evaporation of the solvent followed by recrystallisation from ethanol gave the desired product. Yield 1.54 g (81%), m.p. 192°–195 °C.

$C_{19}H_{15}Cl_3N_4O$ 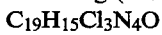

Expected C 54.11, H 3.59, N 13.29, Cl 25.22

Found C 53.94, H 3.74, N 13.44, Cl25.49

EXAMPLE 53

N-(3-(2,6-Difluorobenzyloxy)-pyrid-2-yl-N'-phenylguanidine

(a)
N-(3-(2,6-Difluorobenzyloxy)-pyrid-2-yl-N'-phenylthiourea

A mixture of 2-amino-3-(2,6-difluorobenzyloxy)pyridine (2.1 g, 0.09 mol), phenyl isothiocyanate (1.43 g, 0.011 mol) and toluene (10 ml) was heated under reflux for 3 hours, then cooled and diluted with ether to induce crystallisation of the product, which was recrystallised from ethanol/ether. Yield 2.0 g (82%), m.p. 132°–133 °C.

(b)
N-(3-(2,6-Difluorobenzyloxy)-pyrid-2-yl-N'-phenylguanidine

A mixture of yellow mercuric oxide. (0.75g, 0.0034mol), N-[3-(2-,6-difluorobenzyloxy)pyrid-2-yl]-N'-4-chlorophenylthiourea (1.11 g, 0.003mol) and methanolic ammonia solution (40 ml) was stirred for 15 hours at room temperature. The solvent was removed in vacuo and the black residue was boiled with chloroform and filtered hot. Evaporation of the solvent followed by recrystallisation from ethanol gave the desired product. Yield 0.54 g (51%), m.p. 136°–137 °C.

$C_{19}H_{16}F_2N_4O$ 

Expected C 64.40, H 4.55, N 15.81

Found C 64.16, H 4.73, N 15.81

EXAMPLE 54

N-[3-(2,6-Difluorobenzyloxy)pyrid-2-yl]-N'-(4-chlorophenyl)guanidine

(a)
N-[3-(2,6-Difluorobenzyloxy)pyrid-2-yl]-N'-(4-chlorophenyl)thiourea

A mixture of 2-amino-3-(2,6-difluorobenzyloxy)pyridine (2.10 g, 0.009 mol), 4-chlorophenyl isothiocyanate (1.81 g, 0.01 mol) and toluene (10 ml) was refluxed for 3 hours, then cooled and treated with diethyl ether to induce crystallisation of the product. Yield 2.71 g (75%), m.p. 151°–154 °C.

(b)
N-[3-(2,6-Difluorobenzyloxy)pyrid-2-yl]-N'-(4-chlorophenyl)guanidine

A mixture of yellow mercuric oxide (0.75 g, 0.0035 mol), N-[3-(2,6-difluorobenzyloxy)pyrid-2-yl]-N'-(4-chlorophenyl)thiourea (1.18 g, 0.003 mol) and methanolic ammonia solution (40 ml) was stirred for 2 days at room temperature. The solvent was removed in vacuo and the black residue was boiled with chloroform and filtered hot. Evaporation of the solvent and recrystallisation from acetonitrile gave the desired product. Yield 0.5 g (44%), m.p. 146°–148 °C.

$C_{19}H_{15}ClF_2N_4O$ 

Found C 58.74, H 4.03, N 14.49

Expected C 58.70, H 3.89, N 14.41

EXAMPLE 55

N-(3-(2,4-Difluorobenzyloxy)pyrid-2-yl)-N'-(4-chlorophenyl)guanidine

(a) 2-Amino- 3-(2,4-difluorobenzyloxy)pyridine

A mixture of 2-amino-3-hydroxy pyridine (2.66 g, 0.024 mol), dichloromethane (20 ml) and 40% aqueous sodium hydroxide solution (20 ml) was stirred for five minutes, then 2,4-difluorobenzyl bromide (5.00g, 0.024 mol) and Adogen 464 (3 ml) were added and stirring continued for 16 hours. The mixture was diluted with water and extracted with dichloromethane. Drying and evaporation of the organic extracts, and trituration with ether gave the desired product. Yield 2.7 g (48%), m.p. 105°–107 ° C.

(b) N-(3-(2,4-Difluorobenzyloxy)pyrid-2-yl)-N'-(4-chlorophenyl)thiourea

A mixture of 2-amino-3-(2,4-difluorobenzyloxy)pyridine (2.10 g, 0.009 mol), 4chlorophenyl isothiocyanate (1.81 g, 0.01 mol) and toluene (10 ml) was refluxed for 3.5 hours, then cooled and treated with diethyl ether to induce crystallisation of the product. Yield 2.94 g (81%), m.p.154°–156 ° C.

(c) N-(3-(2,4-Difluorobenzyloxy)pyrid-2-yl)-N'-(4-chlorophenyl)guanidine

A mixture of yellow mercuric oxide (0.75 g, 0.034 mol), N-[3-(2,6-difluorobenzyloxy)pyrid-2-yl]-N'-(4-chlorophenyl)thiourea (1.18 g, 0.003 mol)and methanolic ammonia solution (40 ml) was stirred for 1 day at room temperature. The solvent was removed in vacuo and the black residue was boiled with chloroform and filtered hot. Evaporation of the solvent, trituration with ether and recrystallisation from acetonitrile gave the desired product. Yield 0.91 g (78%), m.p. 182°–184 ° C.
$C_{19}H_{15}ClF_2N_4O$
Expected C 58.70, H 3.89, N 14.41, Cl 9.77
Found C 58.78, H 4.13, N 14.44, Cl 10.12

EXAMPLE 56

N-[3-(2,4,6-Trifluorobenzyloxy)pyrid-2-yl-N'-(4-chlorophenyl)guanidine

(a) 2-Amino- 3-(2,4,6- trifluorobenzyloxy)pyridine

A mixture of 2-amino-3-hydroxy pyridine (2.44 g, 0.022 mol), dichloromethane (20 ml) and 40% aqueous sodium hydroxide solution (20 ml) was stirred for five minutes, then 2,4,6-trifluorobenzyl bromide (5.00 g, 0.022 mol) and Adogen 464 (3 ml) were added and stirring continued for 16 hours. The mixture was diluted with water and extracted with dichloromethane. Drying and evaporation of the organic extracts, and trituration with ether gave the desired product. Yield 2.76 g (49%), m.p. 122°–124 ° C.

(b) N-[3-(2,4,6-Trifluorobenzyloxy)pyrid-2-yl-N'-(4-chlorophenyl)thiourea

A mixture of 2-amino-3-(2,4,6-trifluorobenzyloxy)pyridine (2.29 g, 0.009 mol), 4chlorophenyl isothiocyanate (1.81 g, 0.01 mol) and toluene (10 ml) was refluxed for 3.5 hours, then cooled and treated with diethyl ether to induce crystallisation of the product. Yield 3.03 g (79.5%), m.p.181°–183 ° C.

(c) N-[3-(2,4,6-Trifluorobenzyloxy)pyrid-2-yl-N'-(4-chlorophenyl)guanidine

A mixture of yellow mercuric oxide (0.74 g, 0.036 mol), N-[3-(2,4,6-trifluorobenzyloxy)pyrid-2-yl]-N'-(4-chlorophenyl)thiourea (1.27 g, 0.003 mol) and methanolic ammonia solution (40 ml) was stirred for 1 day at room temperature. The solvent was removed-in vacuo and the black residue was boiled with chloroform and filtered hot. Evaporation of the solvent, trituration with ether and recrystallisation from acetonitrile gave the desired product. Yield 0.63 g (52%), m.p. 161°–162 ° C.
$C_{19}H_{14}ClF_3N_4O$
Expected C 56.10, H 3.47, N 13.77, Cl 8.72
Found C 56.18, H 3.69, N 13.88, Cl 8.85

EXAMPLE 57

N-(3-(2,3,6-Trifluorobenzyloxy)pyrid-2-yl)-N'-(4-chlorophenyl)guanidine

(a) 2-Amino-3-(2,3,6-trifluorobenzyloxy)pyridine

A mixture of 2-amino-3-hydroxy pyridine (2.44 g, 0.022 mol), dichloromethane (20 ml) and 40% aqueous sodium hydroxide solution (20 ml) was stirred for five minutes, then 2,3,6-trifluorobenzyl bromide (5.00 g, 0.022 mol) and Adogen 464 (3 ml) were added and stirring continued for 16 hours. The mixture was diluted with water and extracted with dichloromethane. Drying and evaporation of the organic extracts, and trituration with ether gave the desired product. Yield 2.94 g (53%), m.p. 108°–110 ° C.

(b) N-(3-(2,3,6-Trifluorobenzyloxy)pyrid-2-yl)-N'-(4-chlorophenyl)thiourea

A mixture of 2-amino-3-(2,3,6-trifluorobenzyloxy)pyridine (2.00 g, 0.0078 mol), 4chlorophenyl isothiocyanate (1.6 g, 0.094 mol) and toluene (10 ml) was refluxed for 3 hours, then cooled and treated with diethyl ether to induce crystallisation of the product. Yield 2.82 g (85.5%), m.p.174°–176 ° C.

(c) N-(3-(2,3,6-Trifluorobenzyloxy)pyrid-2-yl)-N'-(4-chlorophenyl)guanidine A mixture of yellow mercuric oxide (1.23g, 0,056 mol), N-[3-(2,3,6-trifluorobenzyloxy)pyrid-2-yl]-N'-(4-chlorophenyl)thiourea (2.00g 0.0047mol) and methanolic ammonia solution (40 ml) was stirred for 1 day at room temperature. The solvent was removed in vacuo and the black residue was boiled with chloroform and filtered hot. Evaporation of the solvent, trituration with ether and recrystallisation from acetonitrile gave the desired product. Yield 1.20 g (63%), m.p. 153°–156 ° C.
$C_{19}H_{14}ClF_3N_4O$
Expected C 56.10, H 3.47, N 13.77, Cl 8.72
Found C 56.09, H 3.68, N 13.80, Cl 8.81

EXAMPLE 58

N-(3-(2-Fluoro-4-methoxybenzyloxy)pyrid-2-yl)-N'-(4-chlorophenyl)guanidine

(a) 2-Amino-3-(2-fluoro-4-methoxybenzyloxy)pyridine

A mixture of 2-amino-3-hydroxy pyridine (1.45g, 0.013 mol), dichloromethane (10 ml) and 40% aqueous sodium hydroxide solution (10 ml) was stirred for five minutes, then 2-fluoro-4-methoxybenzyl bromide (2.9 g, 0.013 mol) and Adogen 464 (1.5 ml) were added and stirring continued for 16 hours. The mixture was diluted with water and extracted with dichloromethane. Drying and evaporation of the organic extracts, and trituration with ether gave the desired product. Yield 1.11 g (34%), m.p. 135°–138 ° C.

(b)
N-(3-(2-Fluoro-4-methoxybenzyloxy)pyrid-2-yl)-N'-(4-chlorophenyl)thiourea

A mixture of 2-amino-3-(2-fluoro-4-methoxylbenzyloxy)pyridine (1.00 g, 0.004 mol), 4chlorophenyl isothiocyanate (0.68 g, 0.0048 mol) and toluene (10 ml) was refluxed for 3 hours, then cooled and treated with diethyl ether to induce crystallisation of the product. Yield0.86g(51%),m.p.138°–140° C.

(c)
N-(3-(2-Fluoro-4-methoxybenzyloxy)pyrid-2-yl)-N'-(4-chlorophenyl)guanidine

A mixture of yellow mercuric oxide (0.54 g, 0.0025 mol), N-[3-(2-fluoro-4-methoxybenzyloxy)pyrid-2-yl]-N'-(4-chlorophenyl)thiourea (0.8 g, 0.0021 mol) and methanolic ammonia solution (40 ml) was stirred for 2 days at room temperature. The solvent was removed in vacuo and the black residue was boiled with chloroform and filtered hot. Evaporation of the solvent followed by trituration with ether and recrystallisation from acetonitrile gave the desired product. Yield 0.37 g, (45%), m.p. 158°–161 ° C.

$C_{20}H_{18}ClFN_4O$
Expected C 59.93, H 4.53, N 13.98, Cl 8.84
Found C 59.63, H 4.66, N 14.13, Cl 8.46

EXAMPLE 59

N-[3-(3-Chloro-2-fluorobenzyloxy)pyrid-2-yl]-N'-(4-chlorophenyl)guanidine (a) 2-Amino- 3-(3-chloro-2-fluorobenzyloxy)pyridine A mixture of 2-amino-3-hydroxypyridine (2.42 g, 0.022 mol), dichloromethane (20 ml) and 40% aqueous sodium hydroxide solution (20 ml) was stirred for five minutes, then 3-chloro-2-fluorobenzyl bromide (5.0 g, 0.022 mol) and Adogen 464 (3 ml) were added and stirring continued for 16 hours. The mixture was diluted with water and extracted with dichloromethane. Drying and evaporation of the organic extracts, and trituration with ether gave the desired product. Yield 3.22 g (58%), m.p. 98°–100 ° C.

(b)
N-[3-(3-Chloro-2-fluorobenzyloxy)pyrid-2-yl]-N'-(4-chlorophenyl)thiourea

A mixture of 2-amino-3-(3-chloro-2-fluorobenzyloxy)pyridine (2.00 g, 0.0079 mol), 4chlorophenyl isothiocyanate (1.61 g, 0.0095 mol) and toluene (10 ml) was refluxed for 3 hours, then cooled and treated with diethyl ether to induce crystallisation of the product. Yield2.37 g (71%),m.p. 174°–176 ° C.

(c)
N-[3-(3-Chloro-2-fluorobenzyloxy)pyrid-2-yl]-N'-(4-chlorophenyl)guanidine

A mixture of yellow mercuric oxide (1.23 g, 0.0047 mol), N-[3-(3-chloro-2-fluorobenzyloxy)pyrid-2-yl]-N'-4-chlorophenylthiourea (2.0 g, 0.0047 mol) and methanolic ammonia solution (40 ml) was stirred for 2 days at room temperature. The solvent was removed in vacuo and the black residue was boiled with chloroform and filtered hot. Evaporation of the solvent followed by trituration with ether and recrystallisation from acetonitrile gave the desired product. Yield 0.38 g (20%), m.p. 204°–207 ° C.

$C_{19}H_{15}Cl_2FN_4O.0.07CHCl_3$
Expected C 55.37, H 3.67, N 13.55, Cl 18.94
Found C 55.36, H 3.81, N 13.55, Cl 18.97

EXAMPLE 60

N-[3-(2-Fluoro-3-methylbenzyloxy)pyrid-2-yl]-N'-(4-chlorophenyl)guanidine (a) 2-Amino-3-(2-fluoro-3-methylbenzyloxy)pyridine A mixture of 2-amino-3-hydroxypyridine (2.8 g, 0.026 mol), dichloromethane (20 ml) and 40% aqueous sodium hydroxide solution (20 ml) was stirred for five minutes, then 2-fluoro-3-methylbenzyl bromide (5.0 g, 0.026 mol) and Adogen 464 (3 ml) were added and stirring continued for 16 hours. The mixture was diluted with water and extracted with dichloromethane. Drying and evaporation of the organic extracts, and trituration with ether gave the desired product. Yield 3.99 g (66%), m.p. 115°–118 ° C.

(b)
N-[3-(2-Fluoro-3-methylbenzyloxy)pyrid-2-yl]-N'-(4-chlorophenyl)thiourea

A mixture of 2-amino-3-(2-fluoro-3-methylbenzyloxy)pyridine (2.00 g, 0.0086 mol), 4chlorophenyl isothiocyanate (1.75 g, 0.0103 mol) and toluene (10 ml) was refluxed for 3 hours, then cooled and treated with diethyl ether to induce crystallisation of the product. Yield 3.21g (93%), m.p. 184°–187 ° C.

(c)
N-[3-(2-Fluoro-3-methylbenzyloxy)pyrid-2-yl]-N'-(4-chlorophenyl)guanidine

A mixture of yellow mercuric oxide (1.29 g, 0.0059 mol), N-[3-(2-fluoro-3-methylbenzyloxy)pyrid-2-yl]-N'-4-chlorophenylthiourea (2.0g, 0.0049 mol) and methanolic ammonia solution (40 ml) was stirred for 2 days at room temperature. The solvent was removed in vacuo and the black residue was boiled with chloroform and filtered hot. Evaporation of the solvent followed by trituration with ether and recrystallisation from acetonitrile gave the desired product. Yield 1.59g, (84.5%), m.p. 179°–181 ° C.

$C_{20}H_{18}ClFN_4O.0.04CHCl_3$
Expected C 61.77, H 4.66, N 14.38, Cl 10.19
Found C 62.04, H 4.79, N 14.53, Cl 10.24

EXAMPLE 61

N-(3-(2,4,6-Trimethylbenzyloxy)pyrid-2-yl)-N'-(4-chlorophenyl)guanidine (a) 2-Amino- 3-(2,4,6-trimethylbenzyloxy)pyridine A mixture of 2-amino-3-hydroxy pyridine (29.6 g, 0.269 mol), dichloromethane (200 ml) and 40% aqueous sodium hydroxide solution (200 ml) was stirred for five minutes, then 2,4,6-trimethylbenzyl bromide (50 g, 0.296 mol) and Adogen 464 (5 ml) were added and stirring continued for 16 hours. The mixture was diluted with water and extracted with dichloromethane. Drying and evaporation of the organic extracts, and trituration with ether gave the desired product. Yield 29.6 g (41%), m.p. 160°–166 ° C.

(b) N-(3-(2,4,6-Trimethylbenzyloxy)pyrid-2-yl)-N'-(4-chlorophenyl)thiourea

A mixture of 2-amino-3-(2,4,6-trimethylbenzyloxy)pyridine (2.00 g, 0.0082 mol), 4chlorophenyl isothiocyanate (1.68 g, 0.0099 mol) and toluene (10 ml) was refluxed for 3 hours, then cooled and treated with diethyl ether to induce crystallisation of the product. Yield 2.37 g (70%), m.p. 180°–182 ° C.

(c) N-(3-(2,4,6-Trimethylbenzyloxy)pyrid-2-yl)-N'-(4-chlorophenyl)guanidine

A mixture of yellow mercuric oxide (0.95 g, 0.0044 mol), N-[3-(2,4,6-trimethylbenzyloxy)pyrid-2-yl]-N'-(4-chlorophenyl)thiourea (1.5 g, 0.0036 mol) and methanolic ammonia solution (40 ml) was stirred for 2 days at room temperature. The solvent was removed in vacuo and the black residue was boiled with chloroform and filtered hot. Evaporation of the solvent followed by trituration with ether and recrystallisation from acetonitrile gave the desired product. Yield 1.16 g (82%), m.p. 169°–171 ° C.

$C_{22}H_{23}ClN_4O$
Expected C 66.91, H 5.87, N 14.19, Cl 8.98
Found C 66.94, H 5.90, N 14.47, Cl 9.17

EXAMPLE 62

N-[3-(2-Chloro6-fluorobenzyloxy)-5-chloropyrid2-yl]-N'-(4-chlorophenyl)guanidine

(a) 2-Amino-N-[3-(2-chloro-6-fluorobenzyloxy)-5-chloropyridine

A mixture of 2-amino-3-hydroxy-5-chloropyridine (1.4 g, 0.313 mol), dichloromethane (5 ml) and 40% aqueous sodium hydroxide solution (5 ml) was stirred for five minutes, then 2-chloro-6-fluorobenzyl chloride (1.96 g, 0.019 mol) and Adogen 464 (0.5 ml) were added and stirring continued for 16 hours. The mixture was diluted with water and extracted with dichloromethane. Drying and evaporation of the organic extracts and trituration with ethanol gave the desired product. Yield 0.93 g (32%), m.p. 132°–133 ° C.

(b) N-[3-(2-Chloro-6-fluorobenzyloxy)-5-chloropyrid-2-yl]-N'-(4chlorophenyl)thiourea A mixture of 2-amino-3-(2-chloro-6-fluorobenzyloxy)-5-chloropyridine (0.82 g, 0.0028 mol), 4-chlorophenyl isothiocyanate (0.56 g, 0.0033 mol) and toluene (10 ml) was heated under reflux for 16 hours, then cooled and diluted with ether to induce crystallisation of the product, which was triturated with ethanol. Yield 0.68 g (54%), m.p. 158°–160 ° C.

(c) N-[3-(2-Chloro-6-fluorobenzyloxy)-5-chloropyrid-2-yl]-N'-(4chlorophenyl)guanidine A mixture of yellow men:uric oxide (0.36 g, 0.0017 mol), N-[3-(2-chloro-6-fluorobenzyloxy)-5-chloropyrid-2-yl]-N'-4-chlorophenylthiourea (0.64 g, 0.0014 mol) and methanolic ammonia solution (20 ml) was stirred for 1 day at room temperature. The solvent was removed in vacuo and the black residue was boiled with chloroform and filtered hot. Evaporation of the solvent followed by recrystallisation from ethanol gave the desired product. Yield 0.09 g (15%), m.p. 162°–163 ° C.

$C_{19}H_{14}Cl_3FN_4O$
Expected C 51.67, H 3.20, N 12.74, Cl 24.19
Found C 51.72, H 3.20, N 12.78, Cl23.11

EXAMPLE 63

N-[3-(2-Chloro-6-fluorobenzyloxy)-6-methylpyrid-2-yl]-N'-(4 chlorophenyl)guanidine

(a) 2-Amino-3-(2-chloro-6-fluorobenzyloxy)-6-methylpyridine

A mixture of 2-amino-3-hydroxy-6-methylpyridine (4.3 g, 0.035 mol), dichloromethane (26 ml) and 40% aqueous sodium hydroxide solution (26 ml) was stirred for five minutes at room temperature, then 2-chloro-6-fluorobenzyl chloride (6.8 g, 0.038 mol) and Adogen 464 (2.5 ml) were added and stirring continued for 16 hours. The mixture was diluted with water and extracted with dichloromethane. Drying and evaporation of the organic extracts and trituration with ethanol gave the desired product. Yield 6.3 g (67%), m.p. 108°–109 ° C.

(b) N-[3-(2-Chloro-6-fluorobenzyloxy)-6-methylpyrid-2-yl]-N'-(4chlorophenyl)thiourea A mixture of 2-amino-3-(2-chloro-6-fluorobenzyloxy)-6-methylpyridine (2.0 g, 0.0075 mol), 4-chlorophenyl isothiocyanate (1.53 g, 0.0089 mol) and toluene (10 ml) was heated under reflux for 2 hours, then cooled and diluted with ether to induce crystallisation of the product, which was triturated with ethanol. Yield 2.6 g (82%), m.p. 204°–205 ° C.

(c) N-[3-(2-Chloro-6-fluorobenzyloxy)-6-methylpyrid-2-yl]-N'-(4chlorophenyl)guanidine A mixture of yellow mercuric oxide (0.58 g, 0.0027 mol), N-[3-(2-chloro-6-fluorobenzyloxy)-6-methylpyrid-2-yl]-N'-4-chlorophenylthiourea (1.00 g, 0.0023 mol) and methanolic ammonia solution (30 ml) was stirred for 2 days at room temperature. The solvent was removed in vacuo and the black residue was boiled with chloroform and filtered hot. Evaporation of the solvent followed by recrystallisation from ethanol gave the desired product. Yield 0.52 g (54%), m.p. 148°–149 ° C.

$C_{20}H_{17}Cl_2FN_4O$
Expected C 57.29, H 4.09, N 13.36, Cl 16.91
Found C 57.34, H 4.20, N 13.39, Cl 17.62

EXAMPLE 64

N-(3-(2,6-Dichlorobenzyloxy)pyrid-2-yl)-N'-methyl-N''-(4-chlorophenyl)guanidine

A mixture of N-[3-(2,6-dichlorobenzyloxy)pyrid-2-yl]-N'-(4-chlorophenyl)thiourea (2.0 g, 0.0045 mol), yellow mercuric oxide (1.18 g, 0.0054 mol) and 33% w/w methylamine in methylated spirit (40 ml) was stirred at room temperature for 24 hours. The solvent was removed in vacuo and the black residue was boiled with chloroform and filtered hot. Evaporation of the solvent and recrystallisation from acetonitrile gave the desired product. Yield 1.53 g (78%), m.p. 153°–156 ° C.

$C_{20}H_{17}Cl_3N_4O$
Expected C 55.13, H 3.93, N 12.86, Cl 24.41
Found C 55.01, H 4.07, N 12.95, Cl 24.50

EXAMPLE 65

N-[3-(2,6-Difluorobenzyloxy)pyrid-2-yl]-N'-methyl-N'-(4-chlorophenyl)guanidine

A mixture of N-[3-(2,6-difluorobenzyloxy)pyrid-2-yl]-N'-(4-chlorophenyl)thiourea (0.93 g, 0.002 mol), yellow mercuric oxide (0.52 g, 0.0024 mol) and 33% w/w methylamine in methylated spirit (45 ml) was stirred at room temperature for 3 days. The solvent was removed in vacuo and the black residue was boiled with chloroform and filtered hot. Evaporation of the solvent, trituration with ether and recrystallisation from acetonitrile gave the desired product. Yield 0.44 g (48%), m.p. 100°–102° C.

$C_{20}H_{17}ClF_2N_4O$
Found C 59.81, H 4.43, N 14.05
Expected C 59.63, H 4.25, N 13.91

EXAMPLE 66

N-(3-(2,6-Difluorobenzyloxy)pyrid-2-yl-N'-(prop-1-yl)-N''-(4-chlorophenyl)guanidine A mixture of N-[3-(2,6-difluorobenzyloxy)pyrid-2-yl]-N'-(4-chlorophenyl)thiourea (1.0 g, 0.0025 mol), yellow mercuric oxide (0.64 g, 0.003 mol) and n-propylamine (20 ml) was stirred at room temperature for 48 hours. The solvent was removed in vacuo and the black residue was boiled with chloroform and filtered hot. Evaporation of the solvent and recrystallisation from acetonitrile gave the desired product. Yield 0.60 g (48%), m.p. 99°–100° C.

$C_{22}H_{21}ClF_2N_4O$
Expected C 61.33, H 4.91, N 13.00, Cl 8.23
Found C 60.78, H 4.95, N 12.96, Cl 8.49

EXAMPLE 67

N-(3-(2,6-Difluorobenzyloxy)pyrid-2-yl-N'-(prop-2-yl)-N-''-(4-chlorophenyl)guanidine A mixture of N-[3-(2,6-difluorobenzyloxy)pyrid-2-yl]-N'-(4-chlorophenyl)thiourea (1.0 g, 0.0025 mol), yellow mercuric oxide (0.64 g, 0.003 mol) and iso-propylamine (0.43 g, 0.0074 mol) in methanol (20 ml) was stirred at room temperature for 96 hours, and then heated at 50° C. for 8 hours. After cooling, the solvent was removed in vacuo and the black residue was boiled with chloroform and filtered hot. Evaporation of the solvent and recrystallisation from acetonitrile gave the desired product. Yield 0.24 g (23%), m.p. 112°–113° C.

$C_{22}H_{21}ClF_2N_4O$
Expected C 61.33, H 4.91, N 13.00, Cl 8.23
Found C 60.34, H 4.93, N 13.10, Cl 8.44

EXAMPLE 68

N-[3-(2-Chloro-6-fluorobenzyloxy)pyrid-2-yl]-N'-methyl-N'-phenylguanidine (a) N-[3-(2-chloro-6-fluorobenzyloxy)pyrid-2-yl)-N-benzoylthiourea A mixture of 2-amino-3-(2-chloro-6-fluorobenzyloxy)-6-methylpyridine (5.0 g, 0.0197 mol), 4-benzoylisothiocyanate (3.8 g, 0.024 mol) and ether (100 ml) was stirred at room temperature for 2 hours, then the solid formed was filtered and washed with pet. ether to give the desired product. Yield 7.31 g (90%), m.p. 136°–138° C.

(b) N-[3-(2-chloro-6-fluorobenzyloxy)pyrid-2-yl-N-benzoyl-N-(methylanilino)guanidine A mixture of N-[3-(2,6-difluorobenzyloxy)pyrid-2-yl]-N'-benzoylthiourea (5.0 g, 0.012 mol), yellow mercuric oxide (3.1 g, 0.014 mol) and N-methylaniline (3.9 ml, 0.036 mol) in methanol (200 ml) was stirred at room temperature for 16 hours, followed by 2 hours at 70° C. The mixture was cooled, the solvent was removed in vacuo and the black residue was boiled with chloroform and filtered hot. Evaporation of the solvent followed by chromatography (silica gel, chloroform) gave the desired product as an oil. Yield 4.73 g (80%).

(c) N-[3-(2-chloro-6-fluorobenzyloxy)pyrid-2-yl]-N-methyl-N-phenyl guanidine

A mixture of N-[3-(2-chloro-6-fluorobenzyloxy)pyrid-2-yl-N-benzoyl-N-(methylanilino)guanidine (0.47 g, 0.00098 mol), hydrochloric acid (2N, 10 ml) and ethanol (3 ml) was refluxed for 16 hours, cooled, filtered and recrystallised from ethanol/ether to give the required product. Yield 0.08 g (20%) m.p. 223°–225° C.

$C_{20}H_{18}ClFN_4O.0.9HCl.0.5H_2O$
Expected C 56.24, H 4.70, N 13.11, Cl 15.78
Found C 56.44, H 4.67, N 12.97, Cl15.82

Biological Data.

$H+K+$ ATPase Activity.

The effects of a single high concentration (100 $\mu$M) of a compound of structure (I) on K-stimulated ATPase activity in lyophilised gastric vesicles was determined. Preferred compounds of structure (I) were also tested over a range of concentrations to determine $IC_{50}$ values.

(i) Preparation of lyophilised gastric vesicles (H/K-ATPase).

Lyophilised gastric vesicles were prepared from pig fundic mucosa after the method of Keeling et. al. (Biochem. Pharmacol., 34, 2967, 1985).

(ii) $K^+$-stimulated ATPase activity.

$K^+$-stimulated ATPase activity was determined at 37° C. in the presence of the following: 10 mM Pipes/Tris buffer pH 7.0, 2 mM $MgSO_4$, 1 mM KCl, 2 mM $Na_2ATP$ and 3–6 $\mu$g protein/ml lyophilised gastric vesicles. After incubation for 30 minutes, the inorganic phosphate hydrolysed from ATP was determined by the method of Yoda and Hokin (Biochem. Biophys. Res. Commun. 40, 880, 1970).

Compounds of structure (I) were dissolved in dimethylsulphoxide which up to the highest concentration used had no effect on $K^+$-stimulated ATPase activity.

The effect of the highest concentration of each compound of structure (I) on the recovery of a standard mount of inorganic phosphate was also determined.

Results

The compounds of the examples exhibited IC50 values of less than 5.5 $\mu$M.

We claim:

1. A compound of structure (I):

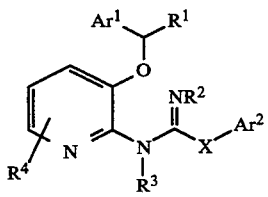

(I)

in which:
Ar¹ is an optionally substituted phenyl ring;
Ar² is an optionally substituted phenyl ring;
R¹ is hydrogen or $C_{1-4}$alkyl;
R² is hydrogen or $C_{1-4}$alkyl;
R³ is hydrogen or $C_{1-4}$alkyl;
R⁴ is hydrogen, halogen, $C_{1-6}$alkyl or $C_{1-6}$alkoxy,
X is $CH_2$ or $NR^5$, and
R⁵ is hydrogen or $C_{1-4}$alkyl, or a salt thereof.

2. A compound according to claim 1 in which R¹ to R⁴ are all hydrogen.

3. A compound according to claim 2 in which Ar¹ is a phenyl ring substituted by two halogen atoms.

4. A compound according to claim 3 in which Ar² is a phenyl ring substituted by a single halogen atom.

5. A pharmaceutical composition comprising a compound according to claim 1 or a pharmaceutically acceptable salt thereof, in association with a pharmaceutically acceptable carrier.

6. A compound according to claim 1 for use in the treatment of gastrointestinal disorders.

* * * * *